(12) United States Patent
Mohr et al.

(10) Patent No.: US 11,262,323 B2
(45) Date of Patent: *Mar. 1, 2022

(54) METHOD FOR IDENTIFYING AND CHARACTERIZING A CONDENSATE ENTRAINED WITHIN A FLUID

(71) Applicant: Mohr and Associates, Richland, WA (US)

(72) Inventors: Charles L. Mohr, Richland, WA (US); Brandt C. Mohr, Richland, WA (US); Benno Mohr, Pullman, WA (US); Michael Stordahl, Kennewick, WA (US); Anthony Cottam, Richland, WA (US); Erik Von Reis, Kennewick, WA (US); Christopher Mulkey, West Richland, WA (US); Ryan Sams, Kennewick, WA (US); Kevin Dawes, Richland, WA (US); Preston May, Richland, WA (US); Duan Nguyen, Richland, WA (US); Daniel Kenney, Richland, WA (US); William Rausch, Richland, WA (US); David Hurley, Pasco, WA (US)

(73) Assignee: Mohr and Associates, Richland, WA (US)

( * ) Notice: Subject to any disclaimer, the term of this patent is extended or adjusted under 35 U.S.C. 154(b) by 736 days.

This patent is subject to a terminal disclaimer.

(21) Appl. No.: 16/131,482

(22) Filed: Sep. 14, 2018

(65) Prior Publication Data

US 2019/0011385 A1    Jan. 10, 2019

Related U.S. Application Data

(63) Continuation-in-part of application No. PCT/US2018/031738, filed on May 9, 2018, and a
(Continued)

(51) Int. Cl.
*G01N 27/02* (2006.01)
*G01N 33/28* (2006.01)

(52) U.S. Cl.
CPC .......... *G01N 27/026* (2013.01); *G01N 27/02* (2013.01); *G01N 33/2823* (2013.01)

(58) Field of Classification Search
CPC ... G01N 27/026; G01N 27/02; G01N 33/2823
(Continued)

(56) References Cited

U.S. PATENT DOCUMENTS 4,786,857 A   11/1988 Mohr et al.
5,723,979 A   3/1998 Mohr
(Continued)

FOREIGN PATENT DOCUMENTS

WO   PCTUS1831738   5/2018

OTHER PUBLICATIONS

Notification of Transmittal of the International Search Report and the Written Opinion of the International Searching Authority, or the Declaration, PCT/US2019/49177, dated Aug. 30, 2019.

*Primary Examiner* — Marrit Eyassu
(74) *Attorney, Agent, or Firm* — Randall Danskin P.S.

(57) ABSTRACT

A method for identifying and characterizing a condensate entrained in a fluid using time domain analysis and frequency domain analysis to identify individual volume fraction constituents and condensates within a pipe on a real time basis and to measure the volume of the individual volume fraction constituents and condensates flowing through the pipe on a real time basis.

19 Claims, 24 Drawing Sheets

Related U.S. Application Data continuation-in-part of application No. 15/172,558, filed on Jun. 3, 2016, now Pat. No. 10,119,850, and a continuation-in-part of application No. 15/173,317, filed on Jun. 3, 2016, now Pat. No. 10,119,929.

(60) Provisional application No. 62/509,080, filed on May 20, 2017.

(58) Field of Classification Search
USPC ............................................. 73/61.44
See application file for complete search history.

(56) References Cited

U.S. PATENT DOCUMENTS

| | | | |
|---|---|---|---|
| 6,144,211 A | 11/2000 | Mohr | |
| 6,348,803 B1 | 2/2002 | Mohr | |
| 10,048,219 B2 | 8/2018 | Mohr et al. | |
| 2003/0122555 A1* | 7/2003 | Baron | G01N 27/221 |
| | | | 324/668 |
| 2006/0081066 A1* | 4/2006 | Drobyshev | G01F 1/7088 |
| | | | 73/861.04 |
| 2009/0126502 A1* | 5/2009 | Wee | G01F 1/74 |
| | | | 73/861.04 |
| 2013/0345994 A1* | 12/2013 | Wiklund | G01F 1/34 |
| | | | 702/46 |
| 2014/0299210 A1* | 10/2014 | Atherton | G01F 1/74 |
| | | | 137/624.27 |
| 2017/0350740 A1 | 12/2017 | Mohr et al. | |
| 2017/0350842 A1 | 12/2017 | Mohr et al. | |

* cited by examiner

METHOD FOR IDENTIFYING AND CHARACTERIZING A CONDENSATE ENTRAINED WITHIN A FLUID

RELATED APPLICATIONS

This application claims priority to, and is a Continuation in Part (CIP) of earlier filed, and currently pending, PCT Application No. PCT/US18/31738 filed on 9 May, 2018, and titled Method for Measuring Multiple Parameters of Drilling Fluid. The entire contents and teachings of said earlier field PCT Application No. PCT/US18/31738 are fully incorporated herein by this reference. Said earlier filed PCT/US18/31738 claims priority to earlier filed (and now expired) U.S. Provisional Application Ser. No. 62/509,080 filed on 20 May, 2017. There is co-pendency with PCT/US18/31738.

This application also claims priority to and is a Continuation in Part (CIP) of earlier filed, and currently pending, U.S. Utility patent application Ser. No. 15/172,558, filed on 3 Jun. 2016, and titled Apparatus for Identifying and Measuring Volume Fraction Constituents of a Fluid. The entire contents and teachings of said earlier filed U.S. application Ser. No. 15/172,558 are fully incorporated herein by this reference. There is co-pendency with U.S. Ser. No. 15/172,558.

This application also claims priority to and is a Continuation in Part (CIP) of earlier filed, and currently pending, U.S. Utility patent application Ser. No. 15/173,317, filed on 3 Jun. 2016, and titled Method for Identifying and Measuring Volume Fraction Constituents of a Fluid. The entire contents and teachings of said earlier filed U.S. application Ser. No. 15/173,317 are fully incorporated herein by this reference. There is co-pendency with U.S. Ser. No. 15/173,317.

On 14 Aug. 2018 the USPTO issued a Notice of Allowance (NOA) for the above identified pending U.S. Utility patent application Ser. No. 15/173,317. On 31 Jul. 2018 the USPTO issued a Notice of Allowance (NOA) for the above identified pending U.S. Utility patent application Ser. No. 15/172,558.

At least one of the named inventors of this utility patent application is also a named inventor in earlier filed PCT/US18/31738, and also a named inventor in earlier filed U.S. Provisional Patent Application Ser. No. 62/509,080, and also a named inventor in the earlier filed U.S. application Ser. No. 15/173,317, and also a named inventor in the earlier filed U.S. application Ser. No. 15/172,558. There is co-inventorship.

TECHNICAL FIELD

This invention relates to a method for identifying, characterizing and measuring condensates entrained in a liquid, and more particularly to a method for identifying, characterizing and measuring volume fractions of "wet gases" entrained within transient "slugs" of liquid periodically released into, and passing through natural gas wells, and related production apparatus, using reflected electrical signals and resonance points.

BACKGROUND OF THE INVENTION

Natural gas is a gaseous mixture comprised of multiple different hydrocarbons and can exist in a gaseous phase as well as liquid phase depending upon temperature and pressure. The most prevalent hydrocarbon within natural gas is methane. The higher the methane concentration, the "drier" or "colder" the natural gas is considered. Other hydrocarbon constituents of natural gas are evaporated liquids such as, but not limited to, ethane, butane, pentane, propane and hexane. These other hydrocarbon constituents are collectively referred to as "condensates" or Natural Gas Liquids (NGL's). The higher the concentration of condensates, or NGLs, the "wetter" or "hotter" the natural gas is considered.

"Condensates" and "NGLs" have significantly higher economic value than methane, and thus "wet gases" are worth considerably more than "dry gases". The market price for condensates, and NGLs, can be many multiples of the market price for methane. Therefore, an accurate assessment and accounting of the volumes of such condensates and NGLs within natural gas is to the economic benefit of well owners and operators.

"Condensates" or "NGL's" must be separated/removed from the natural gas and methane, before the natural gas can be placed in a pipeline and sold/consumed by the general public.

The current practice in the petroleum/fuel industry for identifying measuring the constituents of natural gas and other components being produced by a given natural gas well, or group of natural gas wells, is to separate the produced components in a three phase separator and to identify and measure the produced components individually. Three phase separators are typically large, expensive, maintenance intensive and typically provide production information only after long intervals during which the hydrocarbon components, and other products, separate under the influence of gravity. Furthermore, such three phase separators are generally not operated continuously, but are rather used only during testing and certification of the wells. As such, such three phase separators are not available for periodic and transient releases of wet gases.

The "condensates" are not continuously, evenly, or regularly released into a natural gas well. Instead, such condensates are more commonly periodically and transiently released into a natural gas well as a liquid "slug" wherein the condensates are entrained in water. The occurrence and release of such "slugs" is not predictable, nor regular. Depending upon individual wells, and the geological formations in which the wells are drilled, such slugs may be released/occur as often as multiple times per hour, or as infrequently as only once or twice per several days. Because the "slugs" are primarily liquid, they are highly concentrated volumes of the condensates. (The condensates are in a liquid phase as opposed to a gaseous phase).

The transient and periodic nature of these slug releases exacerbates the problem of identifying and measuring the various condensates comprising the slugs. Three phase separators that are used to provide well certifications, are typically not operated continuously, but rather are only operated periodically during the well certification. The periodic operation of the three phase separators, combined with the periodic and transitory nature of the slug releases has made the accurate and consistent measurement and identification of condensates nearly impossible.

Due to the significantly enhanced economic value of the condensates, as opposed to the methane, it is desirable to be able to accurately identify, characterize and measure the condensates that are periodically and transiently released into natural gas wells so that owners and operators of such wells can be accurately and fairly compensated for the specific hydrocarbons produced by the well.

The instant inventive method herein provides a method for addressing the identification, characterization and measurement of the transient periodic release of the condensates.

A typical periodic and transient release of liquid containing condensates is approximately 200 seconds in duration and the release contains water as well as various liquid and gaseous hydrocarbon components that make up the primary wet gas composition. The volume fractions are at a maximum concentration with the least amount of dilution by methane gas bubbles at the beginning of the transient release. (the slug). The beginning of the transient release provides the most opportune time to make a measurement of the condensate composition. The measurement opportunity is at its best at the beginning of the transient release and will last for a period of approximately two (2) seconds to about seven (7) seconds, calculated from the beginning of the release. The measurement will remain functional throughout the periodic transient release, but the best time to characterize and measure the liquid/condensate composition will be at the beginning of the release. The volume of the release can be measured by the characteristic cross correlation between a first measurement probe and a second measurement probe.

The water/wet gas concentration begins tapering downwardly from the beginning of the release with an increasing amount of methane gas bubbles within the condensate. As the pressure drops, some of the wet gas components will change into the gas phase as the initial liquid slug is dissipated.

The best opportunity for the measurement of the liquid hydrocarbon, versus the water fraction using electric field perturbation, based on time domain reflectometry methods, occurs close to the leading edge of the liquid slug.

Two EFP measurement probes are fixed within a bore of the pipe/conduit a set distance from one another. System pressure and system temperature sensors are also mounted to, and communicate with the fluid within the bore of the pipe/conduit. The sensors are exposed to the fluid flow. The multiphase electronics sampling occurs at approximately 500 frames per second at each of the two EFP probe locations and provides data to characterize the constitutes at each probe station.

Using cross correlation methods, the velocity of the mixture flow within the conduit/pipe can be calculated. Using the average composition calculated from the two EFP measurement probes, the total flow volume and the fractional volume of the hydrocarbon-based constituents and condensates can be estimated. As a result, the total flow and volume of the hydrocarbon-based constituents and condensates can be estimated.

As a result of the slug flow analysis, the characterization of the fractional constituents of the flow, in conjunction with system pressure and temperature, permit an approximation of the fluid density at any point in time. This fluid density measurement may be used in conjunction with an optional external flow measurement device to provide another estimate of the total volume flow of the material through the pipe, which can then be used to improve the resultant calculation of each fluid constituent.

To address the drawbacks of three-phase separators, composition meters have been developed. When a composition meter is combined with a flow meter, production rates for the various components may also be roughly estimated. Composition meters use measurement of dielectric constant, in combination with a density measurement, to determine the volume fractions.

For known composition meters to be consistently accurate, all the dielectric constants and all the densities of the individual produced fluid components must be known for every measurement condition (temperature and pressure). Unfortunately, this is nearly impossible to accomplish because the conditions are continually varying and changing as the well, or group of wells, produce. Accuracy of the measurements is further complicated by several of the lower density hydrocarbon components (for example but not limited to, ethane, propane, butane and pentane) existing in either a liquid state or a gaseous state at pressures between approximately 20 and 250 atmospheres. Further, the produced components are typically at very high temperatures and as a result, produced water boils off into steam within the pipes causing identification and measurements of gaseous components to be particularly difficult because the dielectric constant of steam is very close to the dielectric constants of the lower density hydrocarbon components.

Prior art publications claim it is "impossible" to accurately identify and measure the volume fractions of natural gas without knowing how much of each hydrocarbon constituent is in the liquid or gaseous phase at any given time.

A further complicating factor in measuring volume fraction constituents of mixtures of produced natural gas is the salt content of the mixture. The salt also affects the dielectric constant of the fluid components.

Our method for identifying and characterizing a condensate entrained within a fluid overcomes various of the drawbacks of known methods and apparatus.

SUMMARY OF THE INVENTION

A first aspect of the present invention is a method for identifying, and characterizing a periodic release of a given condensate which is entrained within a source of a fluid, comprising providing a source of a fluid having a given composition which includes a major volume fraction constituent, and wherein the at least one condensate is periodically released, and is then entrained within the source of the fluid, and wherein the major volume fraction constituent, and the at least one condensate each have a previously determined, and known, dielectric constant, and/or a previously determined, and known, resonance point; providing a database having accessible, and stored information about the previously determined, and known dielectric constants of the major volume fraction constituent, and/or the at least one condensate, and accessible and stored information about the previously determined, and known resonance points of given concentrations of the major volume fraction constituent and/or the at least one condensate; providing a probe which is exposed, at least in part, to the source of fluid, and which further has a known length dimension; providing an electrical pulse emitter which, when energized, generates a given electrical pulse which is electrically delivered to the probe, and wherein the electrical pulse electrically travels along the known length dimension of the probe, and further generates an electrical pulse reflection; providing an electrical pulse sampling device which is electrically coupled in electrical pulse receiving, and sensing relation relative to the probe; providing a computer which is electrically coupled with the probe, the electrical pulse emitter, the electrical pulse sampling device, and the database, and wherein the computer determines a time period which elapses between the electrical pulse emission sent into the probe, and the receipt of the sensed electrical pulse reflection received from the probe, and wherein the resonance point of the major volume fraction constituent, and/or the resonance point of the at least one condensate are individually calculated by the computer from the determined time periods, and/or the computer correlates the determined time period to the previously determined, and known, dielectric constants, and wherein the computer then correlates the calculated resonance points of the major volume fraction constituent, and/or the at least one condensate, as provided in the database, so as to identify a characteristic of the major volume fraction constituent, and the at least one condensate which is entrained within the source of fluid; and providing a user interface which is electronically coupled with the computer, and which further generates a user perceivable output which identifies the at least one characteristic of the major volume fraction constituent, and the at least one condensate, respectively.

A second aspect of the present invention is a method wherein the condensate which is entrained within the source of the fluid is transiently, and periodically released, and wherein the method further comprises measuring the transient and periodic release of the fluid entraining the condensate over a given time period.

A third aspect of the present invention is a method wherein the transient, and periodic release of the condensate, and which further is entrained with the source of the fluid, takes place over a time period of less than about 200 seconds.

A fourth aspect of the present invention is a method that further comprises electrically sampling the source of the fluid having the given composition, and which further includes the major volume fraction constituent, and the at least one condensate, during a time period of less than about 7 seconds after the beginning of the given transient, and periodic release of the fluid entraining the condensate.

A fifth aspect of the present invention is a method that further comprises electrically sampling the source of the fluid having the given composition, and which includes the major volume fraction constituent, and the at least one condensate, during a time period when the major volume fraction constituent, which includes the at least one condensate, has the least concentration of a source of methane gas.

A sixth aspect of the present invention is a method wherein the periodic and transient release of the fluid entraining the condensate has a leading edge, and further contains water, and at least one hydrocarbon, each having a predetermined and known resonance point and a predetermined and known dielectric constant, and wherein the method further comprises measuring the volume fraction of the water, and the volume fraction of the at least one hydrocarbon in the periodic and transient release of the fluid entraining the condensate near the leading edge thereof, by employing electric field perturbation which is based, at least in part, upon a time domain methodology.

A seventh aspect of the present invention is a method that further comprises providing an elongated conduit or pipe having an internal bore which has a predetermined, substantially uniform, inside diametral dimension; providing two electric field perturbation probes, and positioning each of the electric field perturbation probes, at least in part, within the bore of the elongated conduit, and at a known, and predetermined distance, one relative to the other; providing a fluid pressure sensor which is mounted in a fluid pressure sensing relationship relative to the internal bore of the elongated conduit, and which further generates a fluid pressure signal; providing a temperature sensor which is mounted in temperature sensing relation relative to the internal bore of the elongated conduit, and which further generates fluid temperature signal; electrically coupling the two electric field perturbation probes, fluid pressure sensor, and temperature sensor in a signal transmitting relationship relative to the computer; delivering the source of the fluid which includes the major volume fraction constituent, and the at least one condensate, into the internal bore of the elongated conduit; electrically sampling, with the computer, each of the respective two electric field perturbation probes, fluid pressure, and/or temperature sensor signals; and correlating the signals received from the at least two electric field perturbation probes, the pressure sensor and/or temperature sensor, with the computer, so as to provide a characterization of the source of the fluid.

An eighth aspect of the present invention is a method wherein each of the electric perturbation sensors are located at predetermined, spaced apart, sensing stations which are located along the elongated conduit, and electrically sampling with the computer, at each of the sensing stations, at a speed of about 500 frames per second.

A ninth aspect of the present invention is a method that further comprises calculating, with the computer, a flow velocity of the source of the fluid through the internal bore of the elongated conduit from the signals received from the two electric field perturbation probes, and the temperature and fluid pressure sensors.

A tenth aspect of the present invention is a method that further comprises characterizing, with the computer, the average composition of the source of the fluid in the region of the respective, spaced, sensing stations by utilizing the signals received from the respective, electric field perturbation sensors; and estimating, by utilizing the computer, a total flow volume of the source of the fluid, and a fractional volume of the at least one hydrocarbon condensate which is entrained with the source of the fluid.

An eleventh aspect of the present invention is a method that further comprises calculating, with the computer, an approximate fluid density of the source of the fluid, by utilizing the signals received from the temperature and pressure sensors, during a given sampling time; and providing an auxiliary, and externally mounted fluid flow measurement device and coupling the auxiliary, and externally mounted fluid flow measurement device in a signal transmitting relationship relative to the computer; delivering the source of fluid to the auxiliary, and externally mounted, fluid flow measurement device, and generating a signal with the auxiliary and externally mounted fluid flow measurement device which is transmitted to the computer; measuring the fluid flowing movement of the source of the fluid through the auxiliary, and externally mounted, fluid flow measurement device; estimating the total flow of the source of fluid, with the computer, by utilizing the signal generated by the auxiliary, and externally mounted, fluid flow measurement device; and improving the estimated calculation of the total flow volume of the source of the fluid, and the fractional volume of the at least one hydrocarbon condensate which is entrained with the source of the fluid, by utilizing the estimated total flow of the source of fluid, and which is detected by the auxiliary, and externally mounted fluid flow measuring device, by employing the computer.

A twelfth aspect of the present invention is a method that further comprises applying a Fourier Transform calculation to the sensed electrical pulse reflection received from the probe, and which is used to determine a resonant frequency and resonance point of at least one of the volume fraction constituents.

A thirteenth aspect of the present invention is a method that further comprises applying a Power Spectral Density (PSD) calculation, by means of the computer, to the Fourier Transform (FFT) frequency so as to determine an amplitude, and strength of at least one of the given resonance points.

A fourteenth aspect of the present invention is a method wherein the volume fraction constituent is a multiplicity of volume fraction constituents.

A fifteenth aspect of the present invention is a method wherein the volume fraction constituents includes a liquid and a gas.

A sixteenth aspect of the present invention is an apparatus that includes a conduit/pipe having a known interior diameter communicating with the source of the fluid so that a volume of the fluid moves through the conduit/pipe at a velocity; a first probe exposed at least in part to the fluid moving through the pipe; a second probe exposed at least in part to the fluid moving through the pipe a known distance downstream from the first probe; a first output generated by the first probe when a volume fraction constituent is sensed by the first probe and a second output generated by the second probe when the same volume fraction constituent is subsequently sensed by the second probe, and wherein the first and second probe outputs are communicated to the computer; and the computer uses a time difference between the first probe output and the second probe output to determine the velocity of the fluid moving through the pipe and by correlating the determined velocity with a known volume of fluid moving through the pipe a volume of the volume fraction constituent is determined by the computer and by correlating the resonance points of the volume fraction constituent to the resonance points for various constituents of volume fraction constituents in the fluid, the volume of the volume fraction constituent is determined.

A seventeenth aspect of the present invention is a method for identifying and characterizing a condensate entrained in a fluid, the method comprising providing a source of fluid, the fluid having a volume fraction constituent condensate entrained in the fluid, and wherein the volume fraction constituent condensate has a previously calculated and known dielectric constant, and previously calculated and known resonance points; providing a database having accessible stored information about the previously calculated and known dielectric constant of the volume fraction constituent condensate and having accessible and stored information about the previously calculated and known resonance points of the volume fraction constituent condensate; providing a probe exposed, at least in part, to the fluid, and wherein the probe has a known length; providing an electrical pulse emitter which electronically generates an electrical pulse which is delivered to the probe, and which further travels the known length of the probe and which generates an electrical pulse reflection; providing an electrical pulse sampler electronically coupled with the probe and which further receives and senses the electrical pulse reflection generated by electrical pulse within the probe; providing a computer electronically coupled with the probe, the electrical pulse emitter, the electrical pulse sampler and the database, and wherein the computer determines a time period between the electrical pulse emission into the probe, and the receipt of the sensed electrical pulse reflection, and wherein the resonance points of the volume fraction constituent condensate are calculated by the computer from the determined time period, and wherein the computer further correlates the determined time period to A previously calculated and known dielectric constant and the previously calculated and known resonance points of the volume fraction constituent condensate as provided in the database to identify the volume fraction constituent condensate in the fluid; and providing a user interface electronically coupled with the computer, and which further generates a user perceivable output which identifies the volume fraction constituent condensate in the fluid.

An eighteenth aspect of the present invention is a method for identifying and measuring a volume fraction constituent condensate of a fluid comprising determining a dielectric constant of a volume fraction constituent condensate moving through a conduit or pipe by determining a time delay between an electrical pulse emission into a probe exposed, at least in part, to the fluid and a reflection of the electrical pulse from the probe; correlating the determined time delay to a database of known dielectric constants of known volume fraction constituent condensates which generate similar time delays to identify the volume fraction constituent condensate; applying a Fast Fourier Transform to the determined time delay to generate a sine wave frequency of the volume fraction constituent condensate; calculating a power spectral density calculation to determine the power and resonance points of the sine wave frequency; correlating the generated resonance points of the volume fraction constituent condensate to a database of known resonance points of known concentration of volume fraction constituent condensates to identify the volume fraction constituent condensate; and providing a user interface which generates a user perceivable output of the identified and measured volume fraction constituent condensates in the fluid in a user perceivable form.

A nineteenth aspect of the present invention further comprises providing a pipe having a known interior diameter that communicates with the source of the fluid so that a volume of the fluid moves through the pipe at a velocity; providing a second probe exposed at least in part to the fluid moving through the pipe a known distance downstream from the first probe; generating a first output by the first probe when a condensate is sensed by the first probe and generating a second output by the second probe when the same condensate is sensed by the second probe, and communicating the first and second probe outputs to the computer; determining a volume of the condensate moving through the pipe by unit of time by calculating a time difference between the first probe output and the second probe output to determine the velocity of the fluid moving through the pipe; and correlating the determined resonance points of the condensate with the database of known resonance points of concentrations of condensates to determine the volume of the condensate moving through the pipe.

BRIEF DESCRIPTIONS OF THE DRAWINGS

DETAILED DESCRIPTION OF THE PREFERRED EMBODIMENTS

Figure 1:
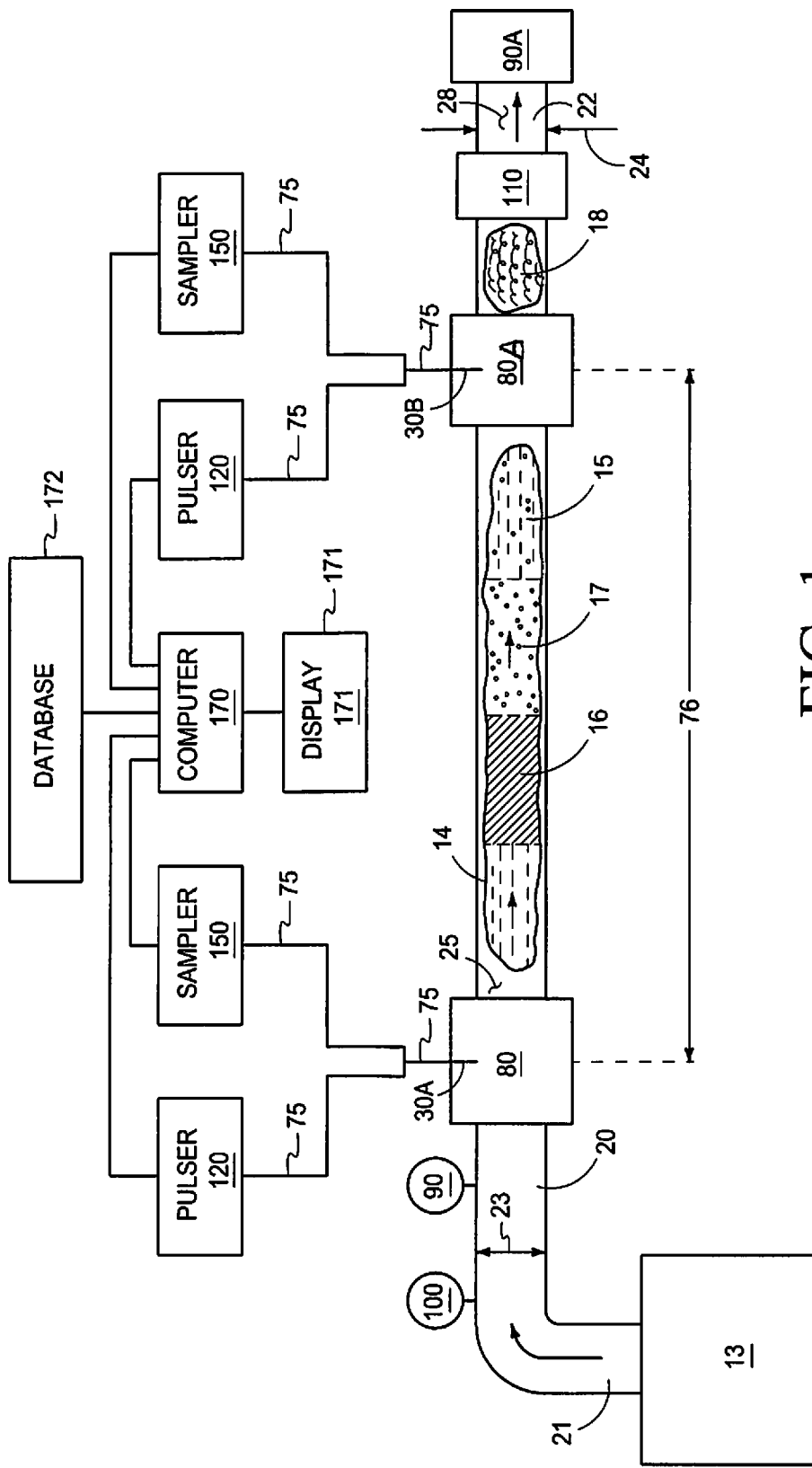
FIG. 1 is a generalized block diagram of our apparatus showing arrangement of the various components and fluid flow therethrough.

This disclosure of the invention is submitted in furtherance of the Constitutional purposes of the U.S. Patent Laws "to promote the progress of science and useful arts" (Article 1, Section 8).

A method for identifying and characterizing a condensate entrained in a fluid generally comprises a source of fluid 13, a conduit or pipe 20, a probe 30, a grayloc support 80, a pulse emitter 120, a pulse sampler 150, a computer 170, a support frame 200, and optionally an externally mounted fluid flow measurement device 90A.

The source of fluid 13 is typically a producing natural gas well, or grouping of natural gas wells producing a fluid 14 that contains a mixture of various volume fractions including, but not limited to, oil 15, water 16, and various forms of hydrocarbon natural gas 17 including, but not limited to, ethane 17A, butane 17B, pentane 17C and propane 17D, and condensate 19. The various hydrocarbon condensates 19 including, but not limited to ethane 17A, butane 17B, pentane 17C and propane 17D may, at least partially comprise, be entrained in the condensate 19, and may also be in the form of an emulsion 18. When produced from the source of fluid 13, the fluid 14 is at pressure and is typically at a temperature that may exceed ambient temperature by hundreds of degrees, although the temperature and pressure vary over time and conditions. It is further contemplated and anticipated the fluid 14 volume fraction constituents 15, 16, 17, 17A, 17B, 17C, 17D, 19 may be produced, and flow through the pipe 20, in segregated fashion, and at other times it is anticipated the volume fraction constituents 15, 16, 17 will be a mixture or emulsions 18 of fluid 14 that may or may not be homogeneously distributed within the pipe 20.

Oil 15, water 16 natural gas 17 and condensate 19 are different molecular compounds, and have different, well recognized dielectric constants and resonance points depending upon the concentration. The dielectric constant of water 16 ranges from approximately 80 for cold water down to approximately 25 for very hot water. The dielectric constant of steam is approximately 1.01 increasing to approximately 1.15 as temperature increases. The dielectric constant of oil 15 is approximately 2.0 to 2.5 depending upon the density of the oil 15. The dielectric constant of natural gas 17 and the various hydrocarbons making up the condensate 19 is approximately 1.2 to approximately 1.8.

Because the known dielectric constant of steam (approximately 1.01-1.15) is similar to the dielectric constant of natural gas 17 and condensate 19 (approximately 1.2-1.8) use of a back pressure regulator 110 communicating with the pipe 20 maintains pressure within the pipe 20 at a pressure at least equal to the pressure of the fluid 14 exiting the source of fluid 13. With the use of a back pressure regulator 110, even though the fluid 14 may be at an extremely high temperature, the water 16 within the fluid 14 will not boil, and will remain in a liquid state with the corresponding dielectric constant and resonance points which are measurably different than the dielectric constant of natural gas 17 and condensate 19. Preventing the formation of steam inside the pipe 20 allows the instant apparatus to distinguish between natural gas 17 and condensate 19, and water 16 using the known dielectric constants and resonance points thereof.

The conduit or pipe 20 has an inflow end 21 communicating with the source of fluid 13 and an outflow end 22 communicating with a distribution point (not shown) such as a collection facility (not shown). The pipe 20 has a known interior diameter 23, an exterior diameter 24, an exterior surface 25, defines a medial channel 28 and may contain a plurality of connections 26 where fittings 27 and apparatus and the like may be joined to the pipe 20, and also where the pipe 20 may connect to other sections of pipe 20 to extend the length thereof.

As shown in FIG. 1, a temperature sensor 100 and a flow meter 90 may be interconnected with the pipe 20 downstream of the source of fluid 13 and upstream of the grayloc support 80. The temperature sensor 100 and flow meter 90 are known apparatus and communicate with the medial channel 28 of the pipe 20 to monitor and sense the temperature of and movement of fluid 14 through the pipe 20. Information and data sensed by the temperature sensor 100 and the flow meter 90 are communicated to the computer 170.

In a first embodiment of the invention (FIG. 2), there are two spaced apart grayloc supports 80, 80A. Each grayloc support 80, 80A (FIGS. 3-5) is a fitting having a "cross" configuration defining an entry port 81, an exit port 82, a probe insertion port 83 and a blind port 84. Each of the ports 81, 82, 83, 84 communicate with a medial chamber 85 therebetween to allow fluid 14 flow therethrough. An exterior circumference of each port 81, 82, 83, 84 defines a radially enlarged sealing flange 86 configured for engagement with a sealing clamp 87 to provide a fluid tight seal between the grayloc support 80 and the adjoining pipe 20, or an adjoining hub 89 to provide fluid containment.

Figure 2:
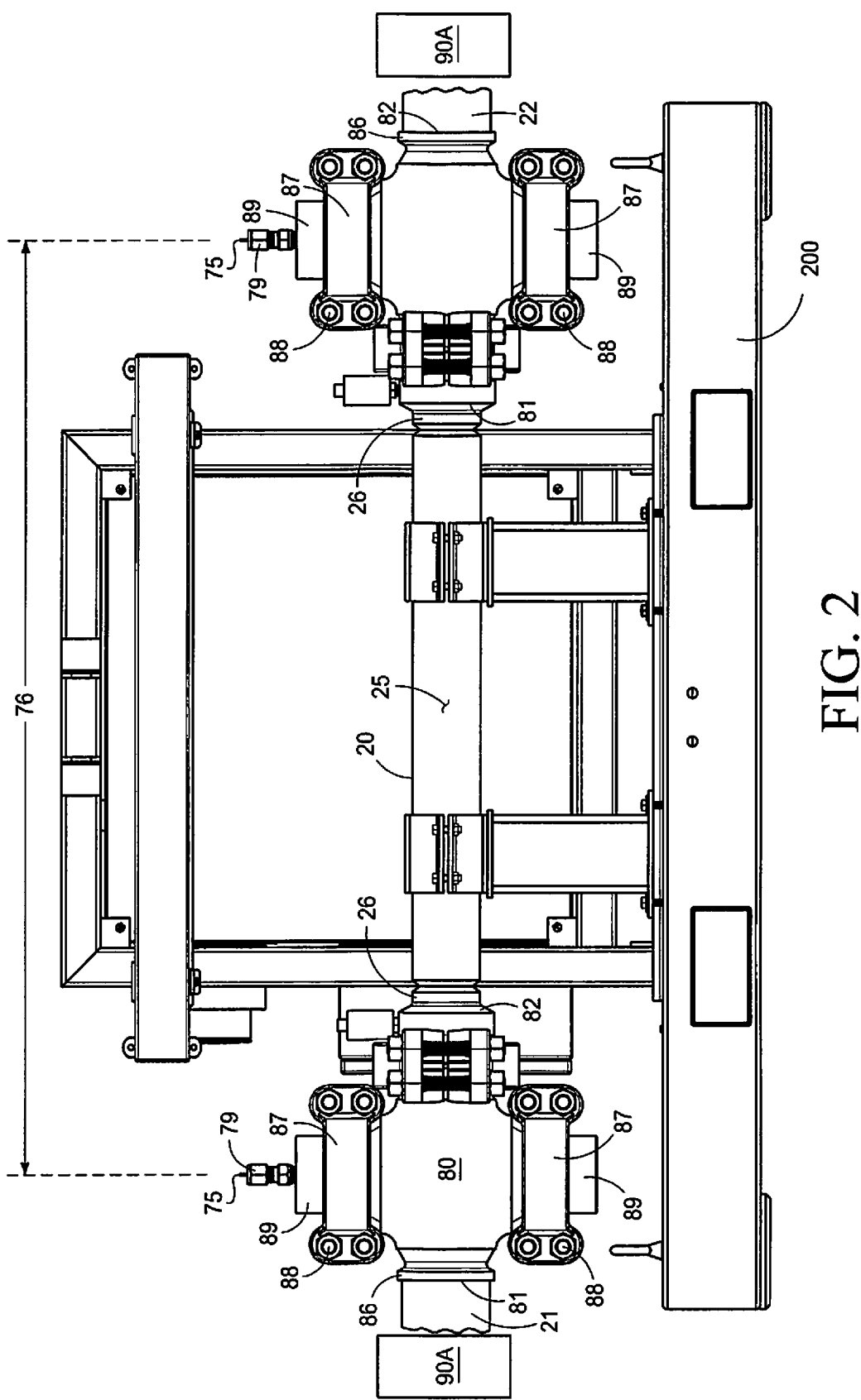
FIG. 2 is an orthographic front view of the two representative spaced apart grayloc supports and an electronics box mounted on a moveable support skid.

As shown in FIG. 2, the second grayloc support 80A communicates with the pipe 20 a known distance 76 downstream from the first grayloc support 80. The second grayloc support 80A has the same components and configuration as the first grayloc support 80 and therefore a detailed description of the second grayloc support 80A is omitted herein.

In the first embodiment there are two spaced apart probes 30A, 30B, one probe 30 within each grayloc support 80, 80A. The first probe 30A and the second probe 30B are identical in configuration, and in function, and therefore only the first probe 30A will be described in detail. These two spaced apart grayloc supports 80 allows velocity and volume to be calculated without use of a flow meter 90, although an external and optional flow meter assembly 90A may be interconnected with the conduit or pipe 20 to provide additional information to the computer 170 to enhance the accuracy of the measurement data, and to provide a separate and independent data point for cross-correlation employing the instant inventive method.

Figure 3:
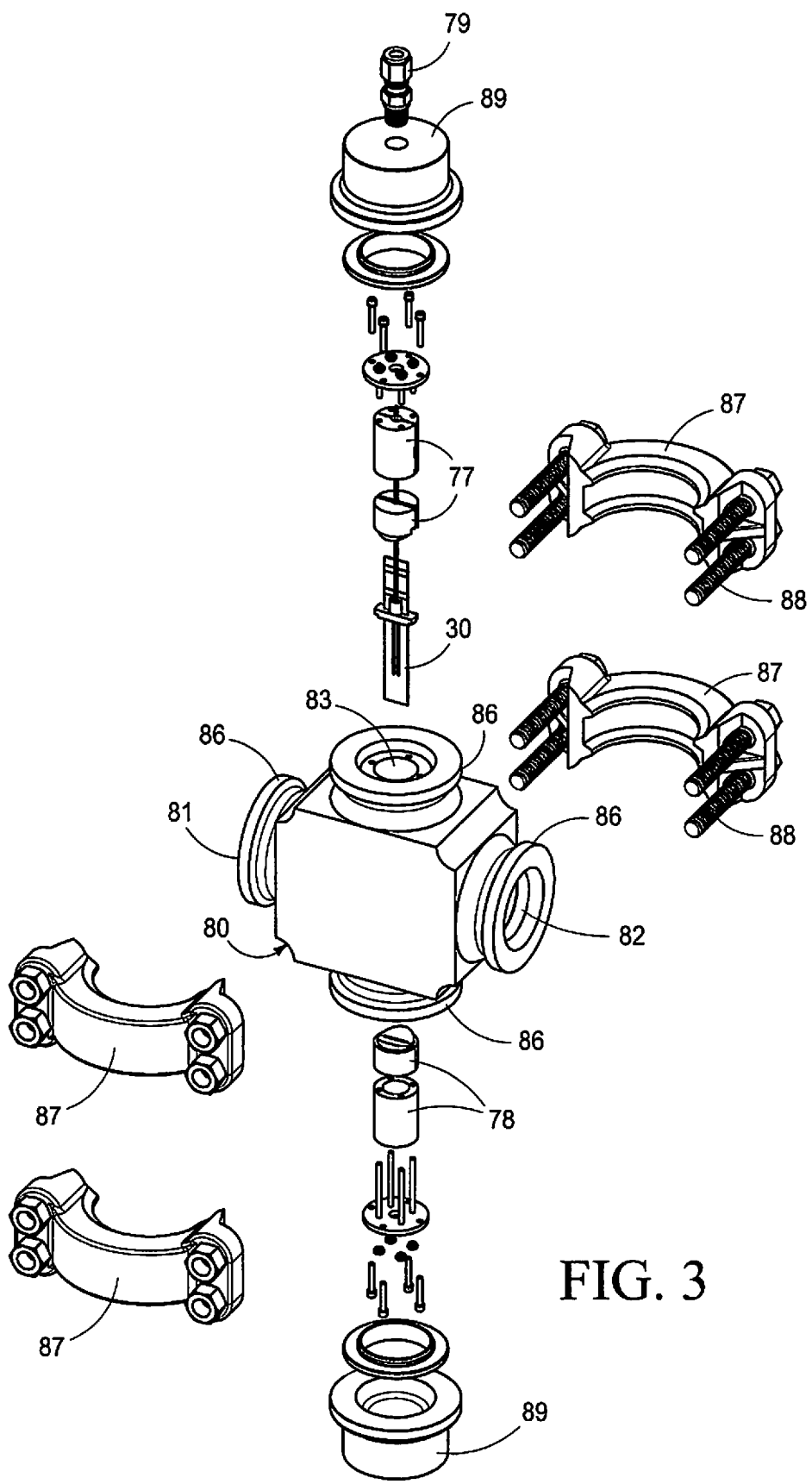
FIG. 3 is an exploded isometric front, side and top view of a grayloc support showing arrangement of the components and the probe.
Figure 4:
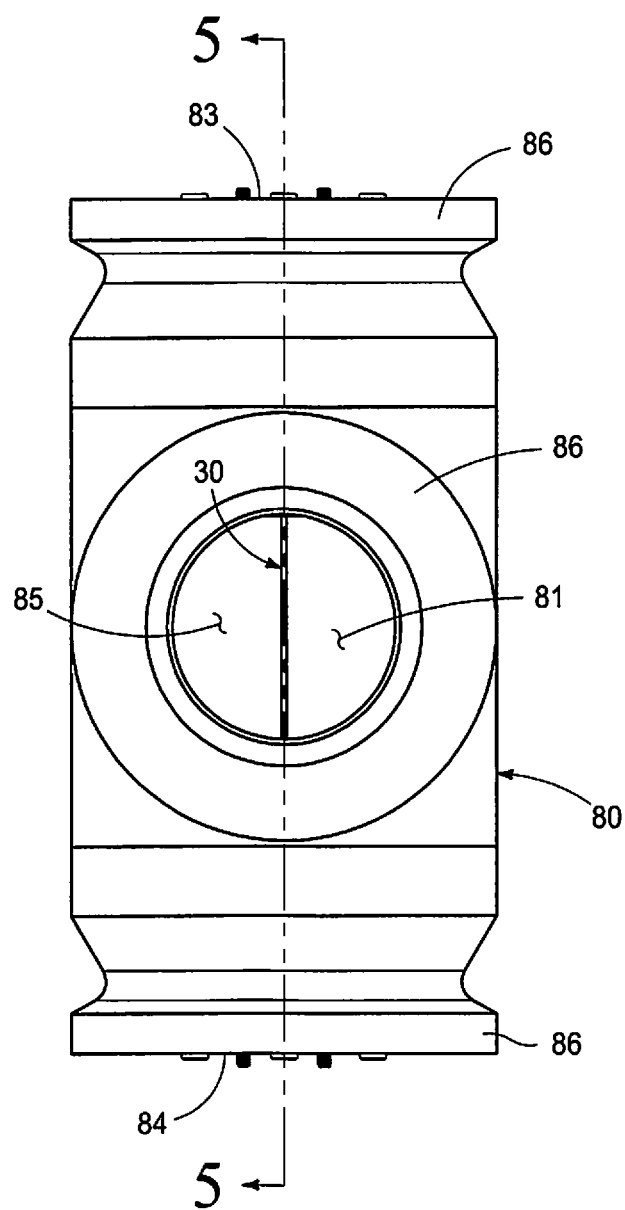
FIG. 4 is an orthographic side view of the assembled grayloc support of FIG. 3, less the sealed hubs.
Figure 5:
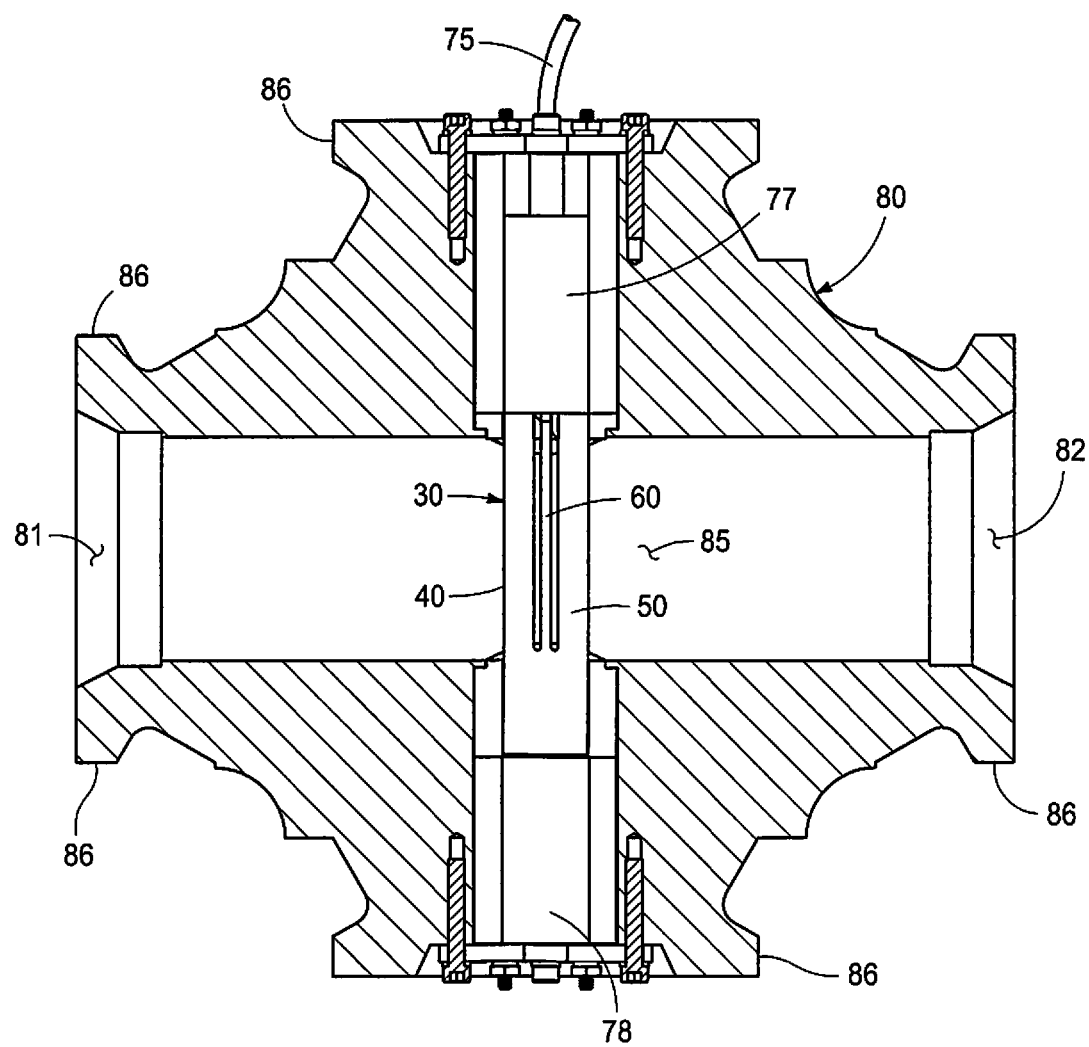
FIG. 5 is an orthographic cross section view of the assembled grayloc support of FIG. 4 taken on line 5-5 from FIG. 4.

As shown in FIGS. 3, 4 and 5, the probe 30 is positionally supported within the medial chamber 85 defined by the grayloc support 80 so that at least a portion of the probe 30 is exposed to the fluid 14 flowing through the grayloc support 80 medial chamber 85.

Figure 7:
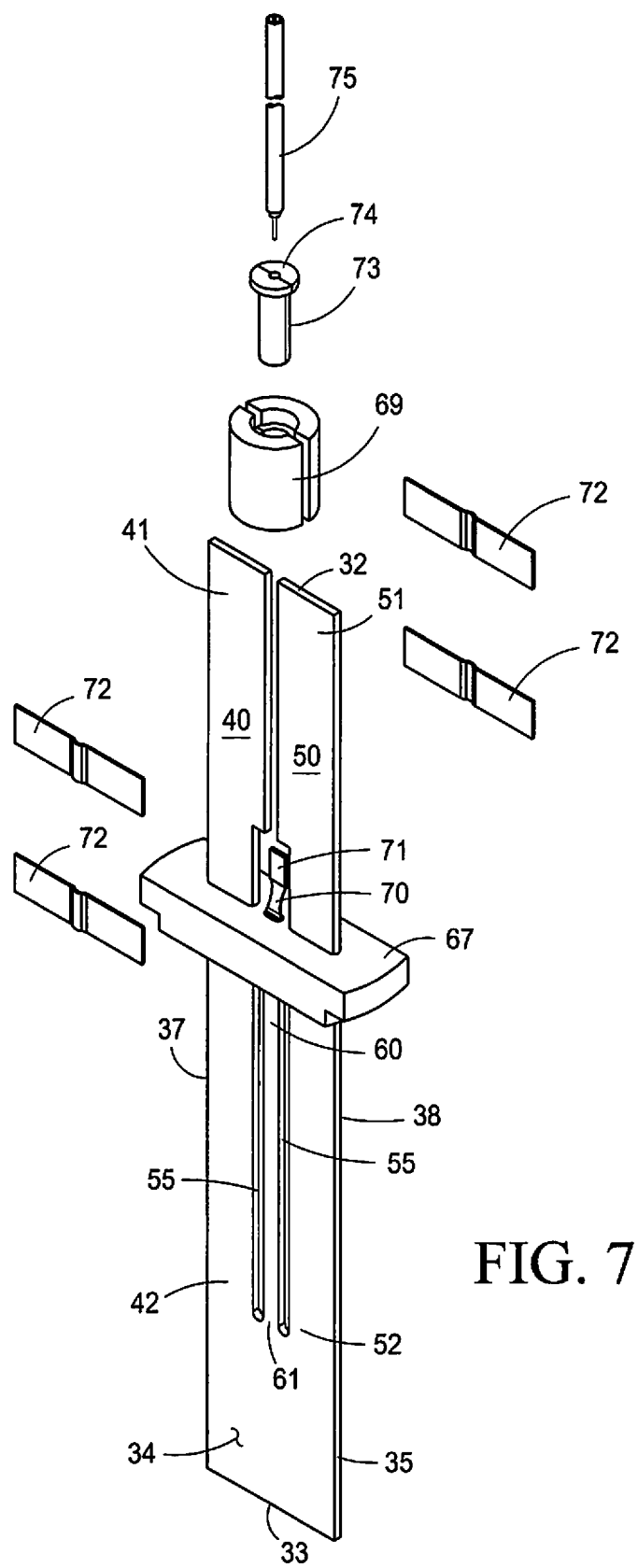
FIG. 7 is an exploded isometric front, side and top view of the probe of FIG. 6.
Figure 8:
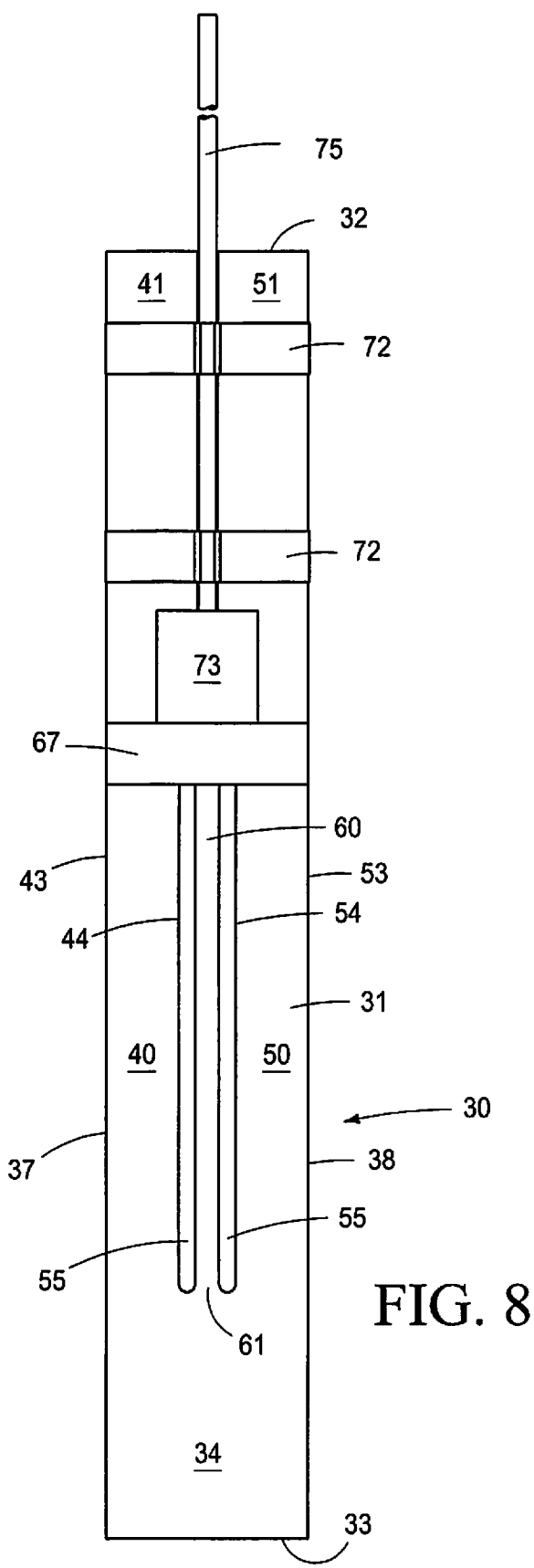
FIG. 8 is an orthographic front view of the probe of FIG. 6 less the support block.

The probe 30 (FIGS. 6-8) has a body 31 that is generally planar and rectilinear. The body 31 has a first end 32 and an opposing second end 33, a first surface 34, and an opposing second surface 35 with a thickness 36 between the first surface 34 and the second surface 35. The body 31 further has a first laterally outer edge 37, and an opposing second laterally outer edge 38 and defines a dimensionally enlarged shoulder (not shown) in the first edge 37 and the second edge 38 spaced apart from the first end 32 to positionally support to a probe support block 67. The body 31 further defines an elongated medial slot 45 between a first ground plate 40 at the first edge 37 and a second ground plate 50 at the second edge 38. An elongated center conductor 60 is carried within the medial slot 45 and has a root end 61 that is structurally attached to the probe body 31 proximate the second end 33 between the first and second ground plates 40, 50 respectively, and the center conductor 60 has a free terminal end 62 within the medial slot 45 proximate to the body 31 first end 32. The free terminal end 62 of the center conductor 60 carries a conductor adaptor link 70 and a conductor weld pad 71 for electronic connection to a coaxial cable 75. The length 66 of the center conductor 60 defines the active length 66 of the probe 30. The first end 32 of the probe body 31 is known as the "active end" of the probe 30.

An elongated gap 55 is defined between each laterally outer edge of the center conductor 60 and a proximate edge of the first ground plate 40 and a proximate edge of the second ground plate 50. The gap 55 is engineered to provide optimum sensitivity to the detection of charges in volume flow constituents 15, 16, 17, 19 by impedance measurements. The gap 55 is uniform along its length and is typically approximately 0.080 inches in width for oil 15, water 16 and natural gas 17 mixtures. It is expressly contemplated however, other gap 55 widths may be used and/or engineered to match the impedances of other volume fraction constituents 15, 16, 17, 19 to be identified and measured in the fluid 14.

A probe support block 67, which is generally rectilinear in configuration and formed of silicon carbide defines a generally medial slot (not shown) therein through which the probe body 31 first end 32 extends. The probe support block 67 frictionally engages with the dimensionally enlarged shoulders (not shown) defined in the probe body 31 so as to positionally maintain the probe 30 relative to the probe support block 67.

A coaxial cable 75 is electronically coupled with the conductor weld pad 71 so that signals may be transmitted to the probe 30 and received from the probe 30. Best shown in FIG. 7, the coaxial cable 75, and its attachment to the conductor weld pad 71, is positionally secured to the probe body 31 by an inner slip support 69, a pack 73 and a ring 74 so that the coaxial cable 75 is securely, and insulatively connected to the center conductor 60. In the current embodiment the pack 73 and ring 74 are formed of TEFLON, but other materials such as PEEK may similarly be used and one contemplated. Plural support straps 72 (FIGS. 8, 9) spacedly arrayed on the probe body 31 further secure the coaxial cable 75 relative to the probe 30.

An active end support 77 (FIG. 3) frictionally engages the first end 32 of the probe 30 and extends over and about the coaxial cable 75 and an inner slip support 69. The active end support 77 aligns and positionally maintains the first end 32 of the probe body 31 within the medial chamber 85 of the grayloc support 80. (See FIG. 5). Similarly, a passive end support 78 frictionally engages with the second end 33 of the probe 30 and similarly aligns and positionally maintains the second end 33 of the probe 30 within the medial chamber 85 of the grayloc support 80. (FIG. 5).

Figure 24:
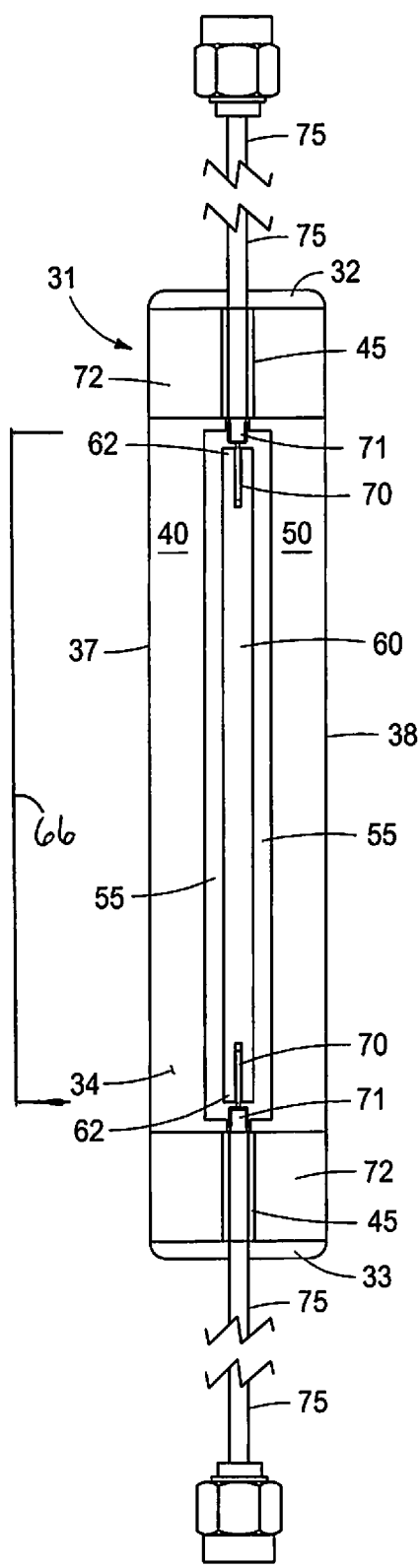
FIG. 24 is an orthographic front view of a third embodiment of an EFP probe, known as a "through" probe.
Figure 25:
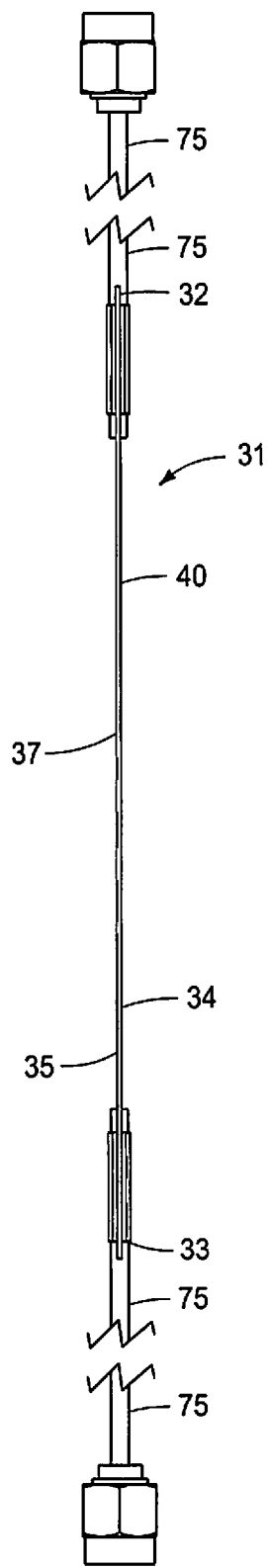
FIG. 25 is an orthographic first side view of the third embodiment of EFP probe of FIG. 24.

When the current design blade probe 30 is utilized the reflected signal (not shown) is electrically returned to the TDR via the coaxial cable 75 and is the sampled reflection. When a double ended or "through" probe 30 (FIGS. 24, 25) is utilized, the signals pass entirely through the active length 66 of the probe 30 from the first end 32 to the second end 33 and the signals are communicated to the pulse sampler 150.

As shown in FIG. 3, the assembled probe 30 and the active end support 77 are inserted into the grayloc support 80 probe insertion port 83 so that a medial portion of the probe 30 extends across the medial chamber 85 and is oriented so that the first surface 34 and second surface 35 are parallel to the flow of fluid 14 through the grayloc support 80 medial chamber 85. The probe 30 and end supports 77, 78 are secured within the grayloc support 80 medial chamber 85 by known means including, but not limited to, a spacer, a retainer plate and alignment pins. Such fastening means secure the first end 32 of the probe 30, and also secure the second end 33 of the probe 30 so that the probe 30 is supported from both the first end 32 and the second end 33 within the medial chamber 85. A fluid tight hub 89 is interconnected with the probe insertion port 83 sealing flange 86, and also with the blind port 84 sealing flange 86. Known sealing clamps 87, and plural threaded fasteners 88 secure the hubs 89 to the sealing flanges 86 to provide a fluid tight seal therebetween. As can be seen in the drawings, the coaxial cable 75 extends through the hub 89 proximate to the first end 32 of the probe 30 by way of a CONAX pressure gland seal 79. The coaxial cable 75 electronically communicates with the probe 30 center conductor 60 and with the pulse emitter 120 and with the pulse sampler 150.

The grayloc entry port 81 communicates with the pipe 20 by means of a fluid tight connection 26 therebetween. Similarly, the exit port 82 communicates with a pipe 20 by means of a fluid tight connection 26 therebetween.

The second grayloc support 80A is also in fluid communication with the pipe 20 a known distance 76 downstream from the first grayloc support 80. The structure of the second grayloc support 80A, and the structure of the second probe 30B carried therein is the same as the aforementioned and described grayloc support 80 and first probe 30A.

The coaxial cables 75 that electronically communicate with each of the probes 30A, 30B are each electronically coupled with a pulse emitter 120 and also with pulse sampler 150. The pulse emitter 120 and the pulse sampler 150 may also be combined into a single apparatus commonly called a Time Domain Reflectometer (TDR), such as the EFP Signal Processor utilizing the CT100B software developed and manufactured by Mohr Test and Measurement of Richland, Wash., USA. Such TDR EFP Signal Processors are described in U.S. Pat. No. 4,786,857 issued Nov. 22, 1998, and U.S. Pat. No. 5,723,979 issued Mar. 3, 1998, and U.S. Pat. No. 6,144,211 issued Nov. 7, 2000, and U.S. Pat. No. 6,348,803 issued Feb. 19, 2002 and which were all invented by Charles L. Mohr (one of the joint inventors herein). The aforementioned issued US patents and the teachings therein are expressly incorporated herein by this reference.

Time domain reflectometry is an effective means for determining the level of a liquid, such as in a tank. Using time domain reflectometry, electrical pulses are conveyed along a transmission line to an electrically conductive probe 30. The electrical pulses are partially reflected when there is a change in the electrical impedance of the fluid 14 to which the probe 30 is exposed. The impedance change is associated with a difference in dielectric strength. "Electrical permittivity" is a technical term indicating the dielectric properties of the fluid 14. The electrical pulses produced by a time domain reflectometry system are affected by the dielectric constant of the surrounding fluid 14 in which the electrical pulse is traveling. The dielectric constant (permittivity) of the fluid 14 directly affects the propagation velocity of an electromagnetic wave as it travels along the probe 30. In time domain reflectometry systems, an electromagnetic pulse is propagated into and along the probe 30 which has a known length while measuring the time of arrival and the time of reflection from electrical discontinuities at two known, spaced apart, points. The first known point is where a coaxial cable 75 is attached to the probe 30. The second known spaced apart point, is a distal end of the probe 30. Since these locations are both known, it is possible to calculate the propagation velocity of the electromagnetic wave and, as a result, calculate the apparent dielectric constant of the material undergoing tests and to which the probe 30 is exposed. Similarly, changes in the dielectric constant which relate to changes in the fluid 14 adjacent to and surrounding the probe 30 can also be determined. For example, the apparent dielectric constant provides a direct indication of the presence of identifiable types of fluids 14 and condensates 19.

The pulse emitter 120 which may be incorporated into a TDR is an electronic apparatus that emits electronic pulses (not shown) which are conveyed to the probe 30 through the coaxial cable 75 at a preferred rate of approximately 500 to 800 samples per second depending upon the speed of computation and generating approximately 500 data points per sample. This means the electronic pulses are at increments of approximately 0.76 picoseconds. When the pulse emitter 120 emits a pulse (not shown) the pulse is conveyed along the coaxial cable 75 and to the probe 30 center conductor 60 through the conductor weld pad 71. The pulse travels along the center conductor 60 whereupon, depending upon the constituents 15, 16, 17, 19 of the surrounding fluid 14 and the respective impedance (dielectric constants) of the constituents 15, 16, 17, 19 to which the probe 30 is exposed, an electrical pulse reflection (not shown) is created when the pulse experiences a change in velocity due to a change in electrical impedance caused by a change in dielectric constant of the fluid 14 within the probe gaps 55 and surrounding the probe 30 active area. The pulse reflection is received from the probe 30 through the coaxial cable 75 and is communicated to the pulse sampler 150 where the reflection is sensed and recorded.

As the dielectric constant properties of the fluid 14 constituents 15, 16, 17, 19 surrounding the probe 30 and within the probe gaps 55 change due to movement of the constituents 15, 16, 17, 19 through the pipe 20, the velocity and distance traveled by the pulse in the increment of time between any two sequential pulses, changes the apparent length of the probe 30. The pulse reflection, which indicates the end of the probe 30 or impedance change (the length of the probe in time), is conveyed along the coaxial cable 75 to the pulse sampler 150. Known computer logic within the computer 170 which is in electronic communication with the pulse emitter 120 and the pulse sampler 150 calculates the "length of the probe in time." Determination of the "length of the probe in time" is empirically representative of the dielectric constant of the fluid constituent 15, 16, 17, 19.

The computer 170 has a database 172, which has stored therein, data and information on predetermined known dielectric constants of fluid constituents 15, 16, 17, 19 and predetermined time delays generated by various dielectric constants. The database 172 also has stored therein predetermined known data and information of resonance points of various known volume fraction constituents 15, 16, 17, 17A, 17B, 17C, 17D, 19 and the resonance points of various concentrations of the volume fraction constituents 15, 16, 17, 17A, 17B, 17C, 17D, 19. The database 172 may also be a correlation or an algorithm wherein information may be correlated and/or compared.

The computer 170 determines the time difference between emission of the electrical pulse into the probe 30 by the pulse emitter 120, and receipt of the pulse reflection from the probe 30, by the pulse sampler 150. The determined time is then correlated by the computer 170, using the database 172 to known predetermined dielectric constants of known volume fraction constituents 15, 16, 17, 17A, 17B, 17C, 17D, 19 which would similarly generate the determined time difference. The correlation of the determined time difference with information contained within the database 172 permits identification of the volume fraction constituent 15, 16, 17, 17A, 17B, 17C, 17D, 19 by "matching" the determined time difference, with the predetermined known dielectric constant of various known constituents 15, 16, 17, 17A, 17B, 17C, 17D, 19 which allows identification of the constituent 15, 16, 17, 17A, 17B, 17C, 17D, 19.

The determined time difference between the electrical pulse emission from the pulse emitter 120 into the probe 30, and receipt of the electrical pulse reflection from the probe 30 by the pulse sampler 150 provides a "length of the probe" measurement which is shared with a detection algorithm within the computer 170 that compares the known "length of the probe" (which correlates to the impedance of the probe 30) to known dielectric constants, which may vary with salt content, and temperature as detected by the temperature sensor 100 in order to match the determined parameters with a known baseline to identify the volume fraction constituents 15, 16, 17, 19 within the fluid 14. This first measure is time domain evaluation. It is the behavior of the electrical pulse within the probe 30, and the resulting length of the probe 30 which allows a first identification of the fluid constituents 15, 16, 17, 19 passing through the grayloc support 80 medial chamber 85. As the fluid 14 passes around and about the probe 30 and through the gaps 55 between the center conductor 60 and proximate edges of the ground plates 40, 50, the pulse reflection, received by the pulse sampler 150 changes as the volume fraction constituents 14, 15, 16, 17, 19 of the fluid 14 change. The change is caused by the changing electrical impedance and changing dielectric constant of the fluid 14 that is in contact with the probe 30 and immediately surrounding the probe 30. However, it is known that the dielectric constants of such volume fraction constituents 15, 16, 17, 19 are variable and dependent upon temperature and salt content and therefore using only one measure does not generate consistently reliably accurate results.

Figure 16:
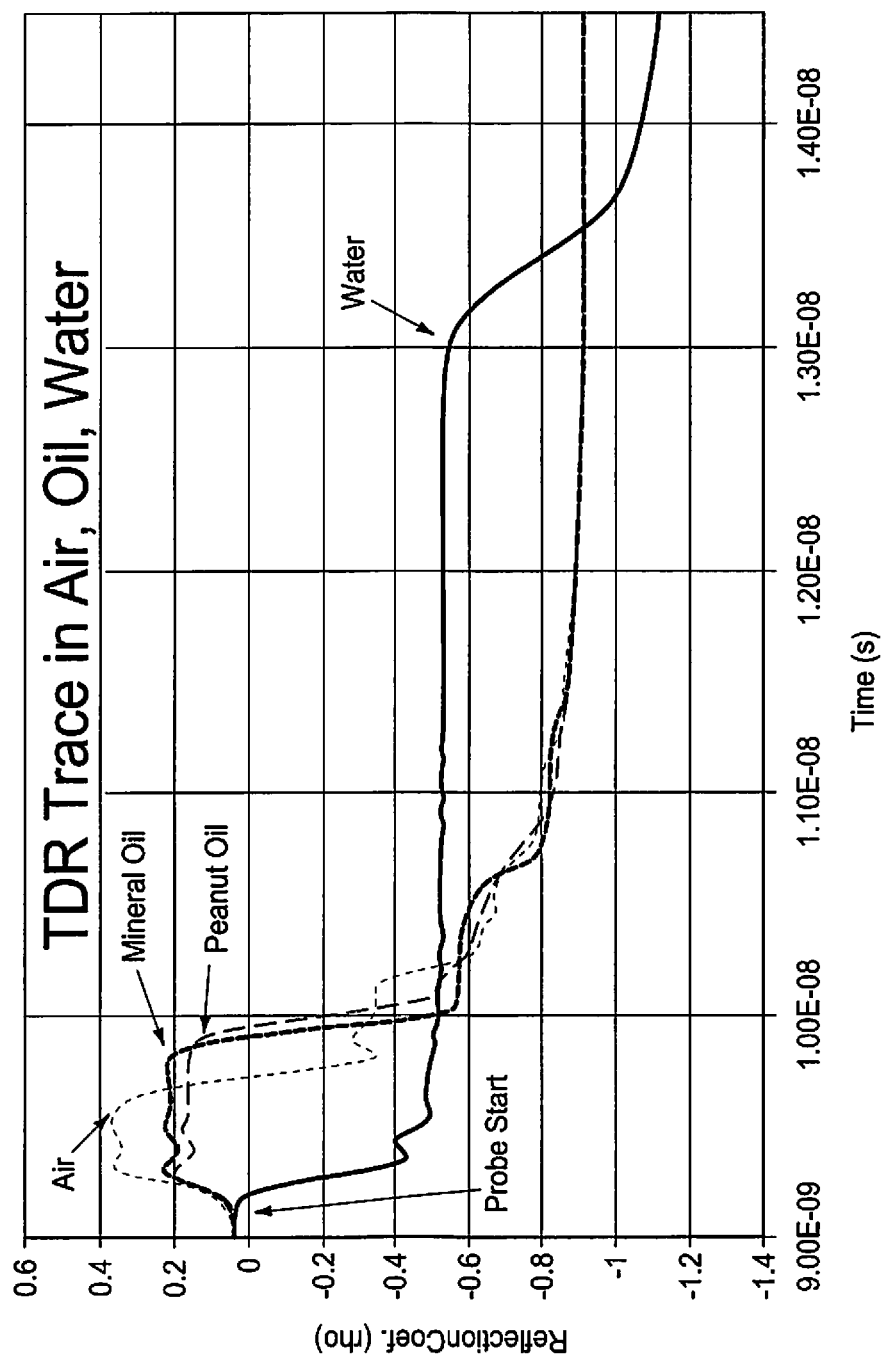
FIG. 16 is a time domain reflectance trace of an electrical pulse through the probe in a mixture of air, mineral oil, peanut oil and water showing the differences in the traces which allows identification of the components.
Figure 17:
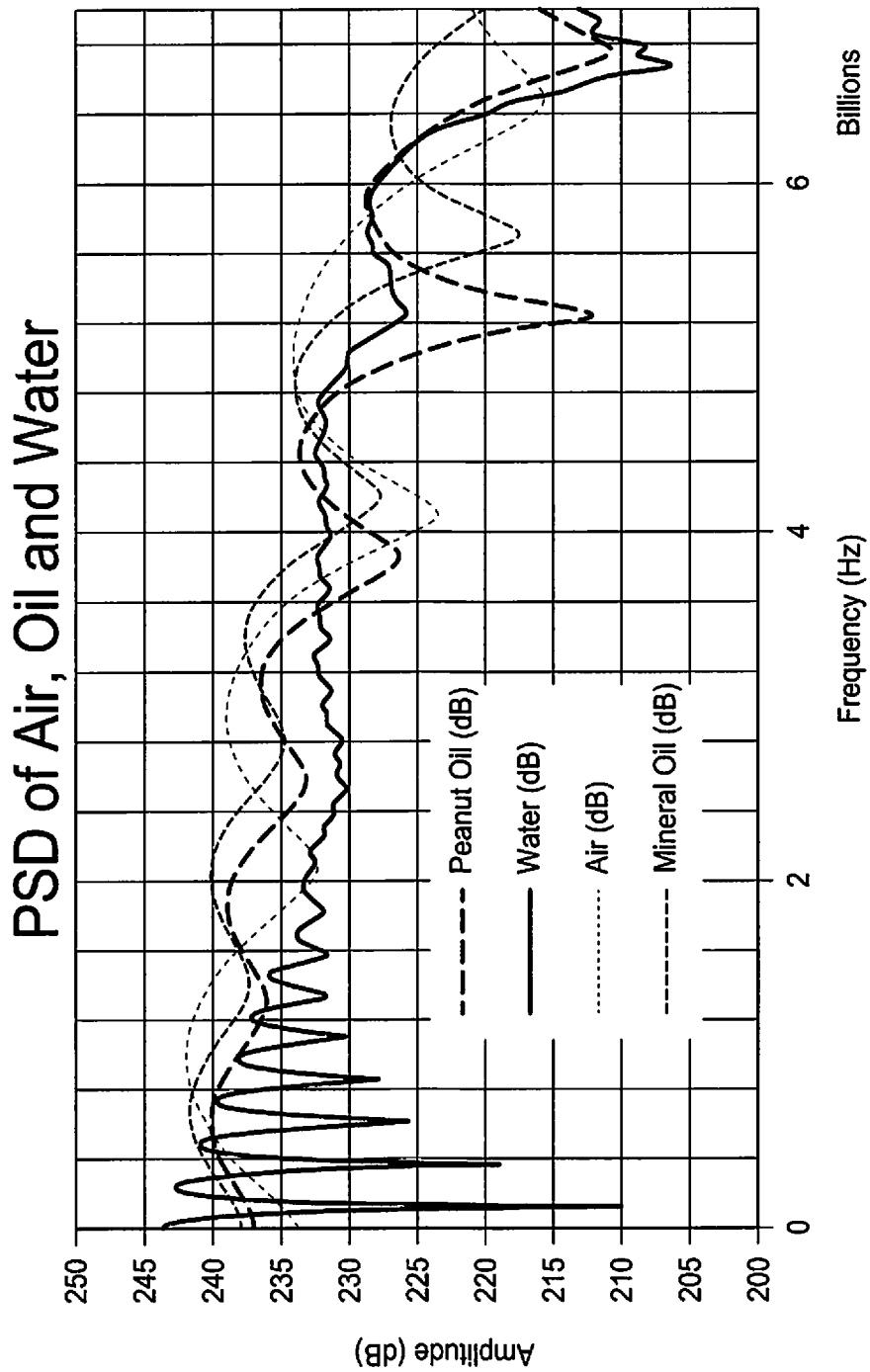
FIG. 17 is a power spectral domain (frequency domain evaluation) graph of the TDR traces of FIG. 16 after applying the FFT and PSD showing the resonance points of the components.
Figure 18:
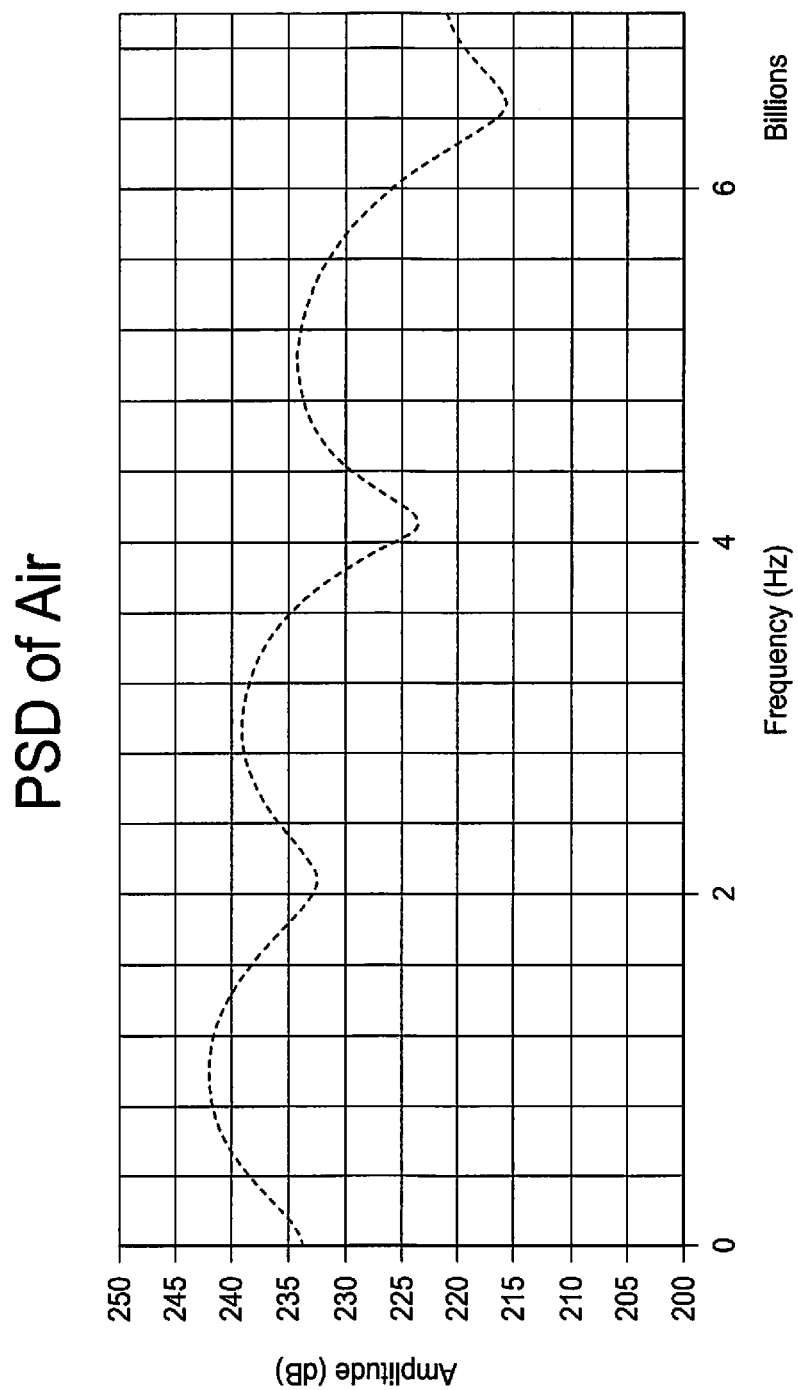
FIG. 18 is a power spectral domain (frequency domain evaluation) graph of the TDR trace of FIG. 11 showing the resonance points in air.
Figure 19:
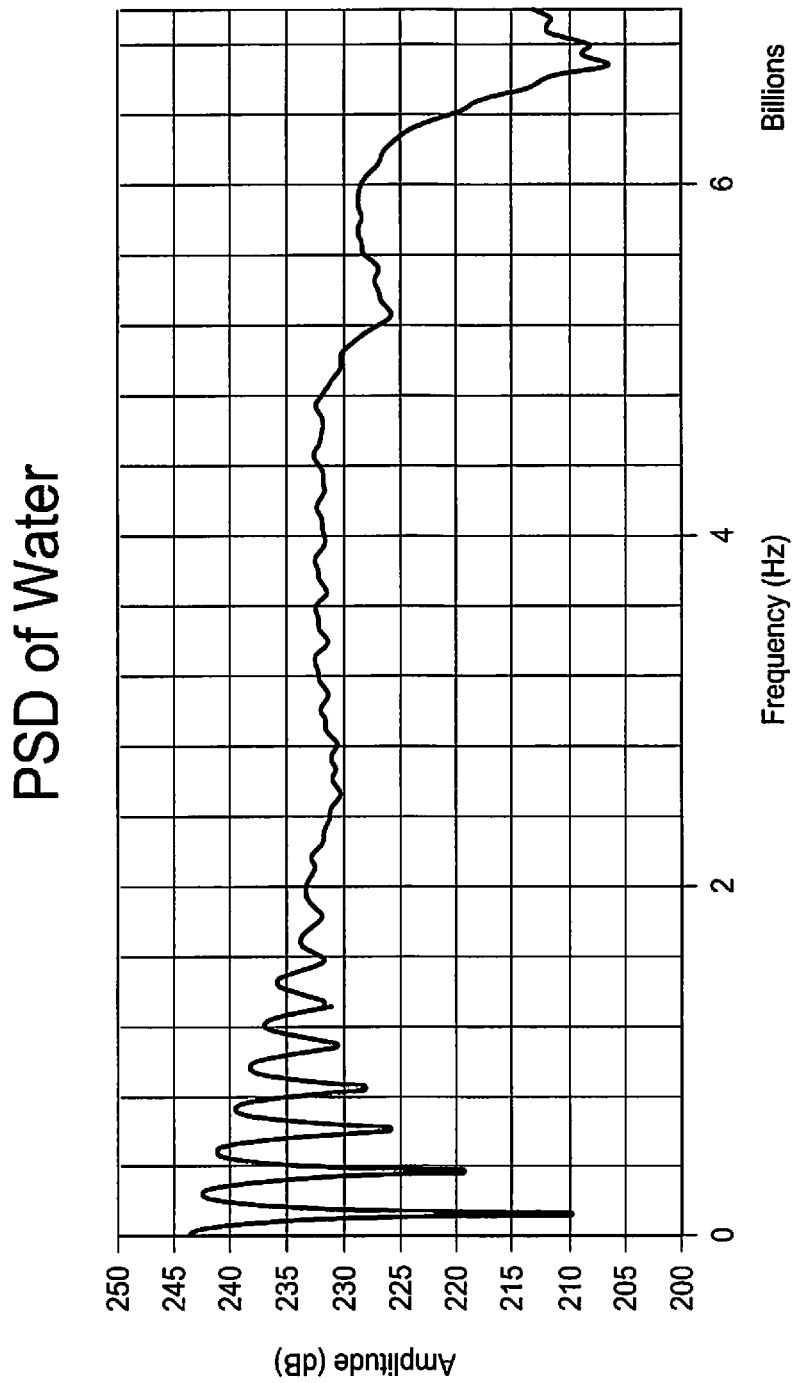
FIG. 19 is a power spectral domain (frequency domain evaluation) graph of the TDR trace of FIG. 12 showing the resonance points in water.
Figure 20:
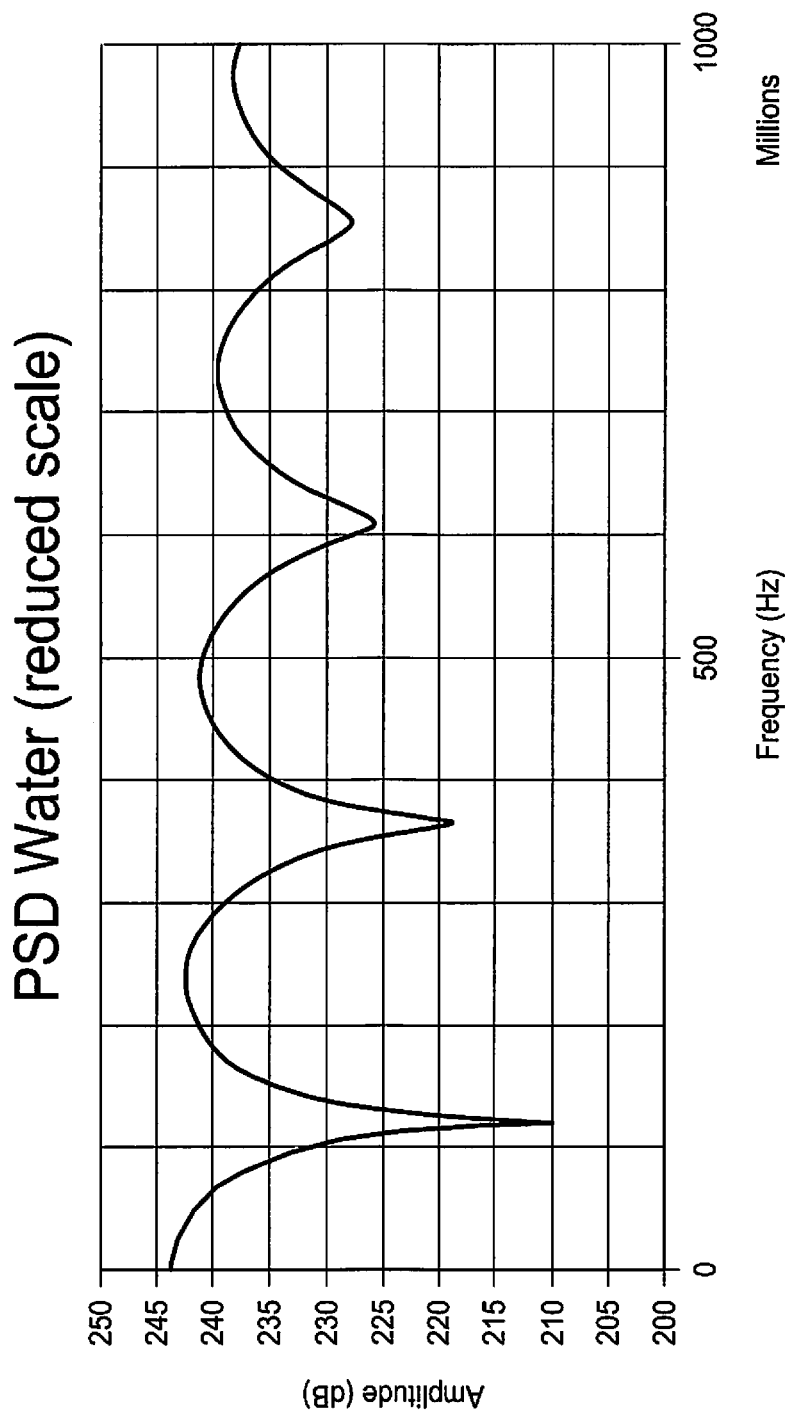
FIG. 20 is a reduced scale power spectral domain (frequency domain evaluation) of the probe in water, similar to that of FIG. 19 showing the resonance points.
Figure 21:
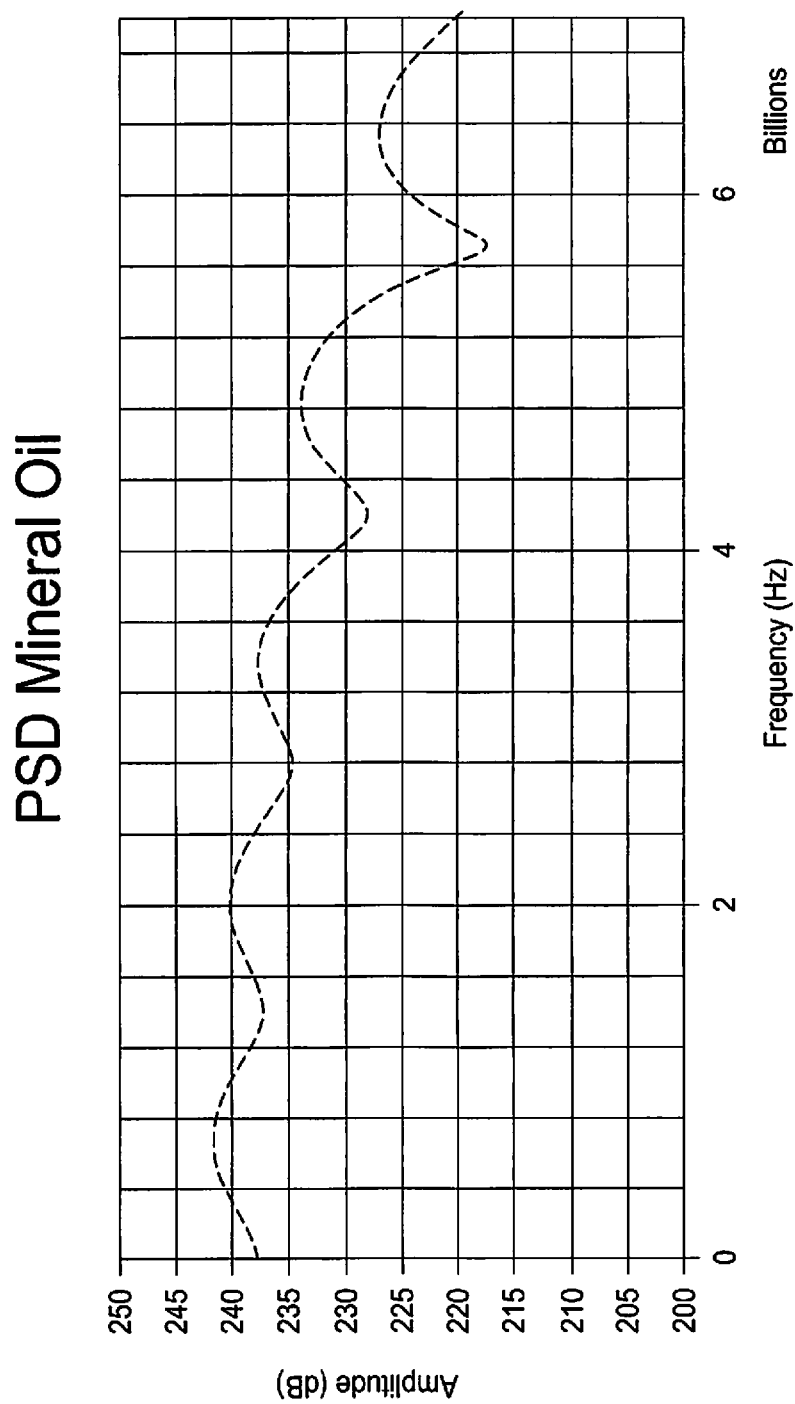
FIG. 21 is a power spectral domain (frequency domain evaluation) graph of the TDR trace of FIG. 13 showing the resonance points in mineral oil

A second, frequency domain analysis takes advantage of the resonance of an electrical signal in the fluid 14 and allows measuring of a volume of the volume fraction constituent 15, 16, 17, 19 within the fluid 14. By performing a Fourier Transform (FT) of the pulse reflection, a sine wave frequency is determined. The frequency and amplitude of the sine wave signal (Power Spectral Density PSD) as a function of frequency allows different characteristic patterns of the constituents 15, 16, 17, 19 to be identified. By examining the various resonance points as the frequency increases, the distance between the resonance points and the amplitude (strength) of the resonance points provide additional information as to various hydrocarbon constituents within the fluid 14 and allows identification and characterization of those various components, and other components which may be newly appearing in the fluid 14 passing by the probes 30A, 30B. FIG. 16 shows the combined signals from a probe 30 in water 16, mineral oil, peanut oil and air. (Peanut oil and mineral oil were used in testing as representative oils to replicate petroleum). FIG. 17 shows the FT transform of the same signals taken from the probe 30 in the different fluids 14 showing the Power Spectral Density (PSD) as a function of the frequency. As can be seen, the frequency/amplitude points of water 16, oil 15, air and peanut oil are distinctly different from one another, and changes in the relative fractions of the composition (concentrations) of the oil 15 causes a resulting shift in the resonance. The shift in resonance allows a measure of the fraction of each of the volume fraction constituents 15, 16, 17, 19.

By performing the Fourier Transform (FT) of the reflected electrical pulse received by the pulse sampler 150, and by performing a Power Spectral Density (PSD) calculation, the frequency and amplitude of the resonance points can be identified.

The FT takes a time-based plot (the determined time delay) and converts the time-based plot into a series of sine waves that duplicate the time history of the electric pulse as a series of frequency based sine waves with the maximums and minimums of the sine waves representing amplitude and resonance points of the volume fraction constituents 15, 16, 17, 19 to which the probe 30 is exposed during the pulse and reflection thereof. The PSD calculation determines the average power, amplitude and frequency of the FT transform. The first resonance point is identifiable because it has a wavelength that is equal to twice the active length of the probe 30. The relative permittivity of the fluid 14 is calculated by comparing the determined velocity of the pulse in the fluid constituents 15, 16, 17, 19 to the velocity of light in a vacuum using the following relationship between velocity and dielectric:

$$\frac{cf}{c} = \sqrt{1/ef};$$

where cf is the transmission speed of the pulse in the fluid 14, c is the speed of light in a vacuum, and ef is the relative permittivity or dielectric constant of the fluid 14. It is further noted that an inverse of the FT allows recreation of the time history plot.

FIG. 16 shows combined time delay signals from a probe 30 exposed to water 16, oil 15 and air. The time delay shown in FIG. 16 is the transit time for the pulse to reach the end of the probe 30 and reflect therefrom. This time delay is proportional to the dielectric constant of the constituents 15, 16, 17, 19 surrounding the probe 30. FIG. 17 shows a graphed Fourier Transform and PSD of the signals shown in FIG. 16. FIG. 17 also shows the resonant peaks generated by the probe 30 in air, water 16 and oil 15.

As can be seen in FIG. 16, the dielectric constants are all different from one another, and changes in the relative volume fractions 15, 16, 17, 19 causes a shift in the resonance peaks.

As shown in FIGS. 1 and 2, a second grayloc support 80A is interconnected with the pipe 20 a known distance 76 downstream from the first grayloc support 80. The second downstream grayloc support 80A carries a second probe 30B that is identical in configuration and function to the first probe 30A. The second probe 30B is similarly electronically coupled with a pulse emitter 120 and also with a pulse sampler 150, or a combined TDR. (Not shown). The pulse emitter 120 and pulse sampler 150 perform the same functions as the previously identified pulse emitter 120 and pulse sampler 150 to determine a time delay between the pulse emission into the probe 30B and receipt of a pulse reflection from the probe 30B by the pulse sampler 150. The determined time delay allows determination of the dielectric constants of the constituents 15, 16, 17, 19 of the fluid 14 by comparison to the known, pre-determined time delay information stored in the database 172 information that is assessable by the computer 170. Each probe 30A, 30B may be, coupled with, a separate pulse emitter 120 and a separate pulse sampler 150 which as noted previously may be combined within a single TDR. (not shown). The computer 170, and the database 172 accessible thereby, is electronically coupled with both pulse emitters 120 and both pulse samplers 150 (both TDR's) so as to correlate the determined time delays from each probe 30A, 30B with the information within the database 172.

The known distance 76 between the first probe 30A and the second probe 30B allows the instant invention to continuously, and in real time, determine the volume of each volume fraction constituent 15, 16, 17, 19 moving through the pipe 20. Because the computer 170 is electronically coupled with the first probe 30A and with the first pulse emitter 120, and the first pulse sampler 150, and also with the second probe 30B and the second pulse emitter 120, and the second pulse sampler 150, the computer 170 is able to determine a time delay between the first probe's 30A identification of a specific volume constituent 15, 16, 17, 19 and the second probe's 30B identification of the same volume constituent 15, 16, 17, 19 subsequent to the first probe 30A identification. Because the interior diameter 23 of the medial channel 28 is known, the total volume of the fluid 14 moving through the pipe 20 by unit of time may be calculated once the velocity of the fluid 14 in the pipe 20 is determined. The time delay between the first probe 30A identifying a specific volume constituent 15, 16, 17, 19 and the second probe 30B subsequently identifying the same volume constituent 15, 16, 17, 19 is used in conjunction with the known distance 76 and known volumetric formulas to determine the volume of identified volume fraction constituents 15, 16, 17, 19 moving through the pipe 20. The probe's 30A, 30B detection of a change in probe length, as described earlier, is indicative of a different volume fraction constituent 15, 16, 17, 19 being identified by the probe 30A, 30B and that information, which is communicated to the computer 170 allows identification of the volume constituent 15, 16, 17, 19, and the volume of the volume of that constituent 15, 16, 17, 19 to be determined.

The time domain evaluation, and the frequency domain evaluation, provide two separate methods to identify volume fraction constituents 15, 16, 17, 19 in the fluid 14 and further allows a determination of a volume of each volume fraction constituent 15, 16, 17, 19 to be determined as the fluid 14 moves through the pipe 20, on a continuous basis. The frequency domain evaluation further allows the concentration of the various volume fraction constituents 15, 16, 17, 19 in the fluid 14 to be determined by correlating the resonance points of the fluid constituents with known resonance points of known constituent concentration within the database 172.

Each probe 30A, 30B has a probe body 31 (FIGS. 6-10) that is generally rectangular in shape and formed of a metallic alloy and is preferably approximately 0.050 inches thick from the first surface 34 to the second surface 35 and approximately 1.00 inches in width from the first edge 37 to the second edge 38. The probe body 31 is preferably formed entirely of INCONEL® alloy 725 which is highly resistant to the corrosive environment to which the probe body 31 may be exposed during operation. Further, a desirable and durable dielectric oxide coating (not shown) is formed on the probe of body 31 extending entirely thereabout. INCONEL® alloy 718 may also be used, but INCONEL® alloy 725 is preferred. INCONEL® alloy 725 and INCONEL® alloy 718 are available from Megamex Specialty Metals of Humble, Tex.

The method of forming the probe 30, which carries the durable dielectric oxide coating on its outer surfaces 34, 35, includes the steps of cutting the desired probe 30 shape from the desired metallic alloy and then oxidizing cleaning the probe body 31 at approximately 1,750° to 2,000° Fahrenheit in air for one to three hours in order to form the highly electrically resistive oxide surface covering the entire body 31 of the probe 30. The temperatures used in formation of the oxide coating reduce cracking of the oxide coating and prevents embrittlement caused by grain growth. Following the one to three-hour heat treatment, the probe body 31 is cooled to less than 1,000° Fahrenheit. Subsequently, the probe body 31 is heated in air to 1,325° Fahrenheit for a period of about 8 hours. Thereafter, the probe body 31 is air cooled in an oven to ambient temperature. The heat treatment process forms a chrome alumina oxide coating covering the entire probe body 31 to insulate the probe body 31 in the fluid 14. The oxide coating is preferably approximately 0.5 mm to approximately 3 mm thick and is believed to have a chemical composition of approximately CrMoNbTiAl.

It is desirable that the probe body 31, carrying the chrome alumina oxide coating has an impedance of approximately 90 ohms in air, which allows use of a 90-ohm coaxial cable 75 for interconnection with the pulse emitter 120 and the pulse sampler 150. The use of a 90-ohm coaxial cable 75 allows the probe 30 to measure 100% water 16; water 16 containing very little oil 15; 100% oil 15; and oil 15 containing very little water 16. Providing for such a wide range of measurements of water/oil/gas/condensate mixtures allows the probe 30 to measure a full range of "water cuts". Further, the ability to operate at 90 ohms allows the probe 30 to identify drilling fluids (not shown) and components thereof and also identify and measure effective water 16 content within drilling fluids. The probe's 30 the ability to measure water content allows the probe 30 to be used in stationary operations, such as to measure the water 16 content of a standing pool of fluid 14, such as fuel in a fuel tank (not shown) that may be contaminated with an unknown amount of water 16. The ability to detect and measure moving/flowing fluids allows the instant invention and probes 30 to be used in the drilling of hydrocarbon producing wells, as well as the use in hydrocarbon producing wells that are in production.

Figure 6A:
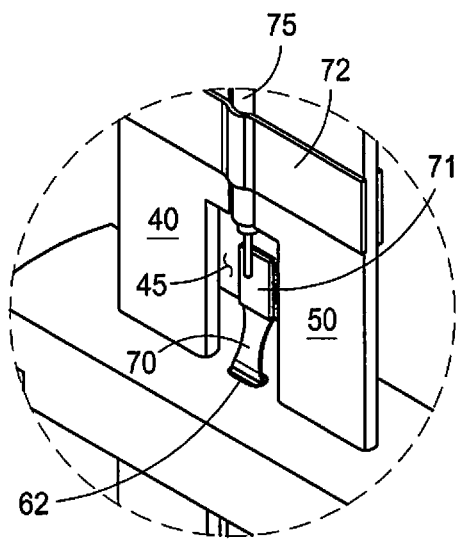
FIG. 6A is an enlarged isometric view of the probe and support block showing details of the coaxial cable connection.
Figure 6:
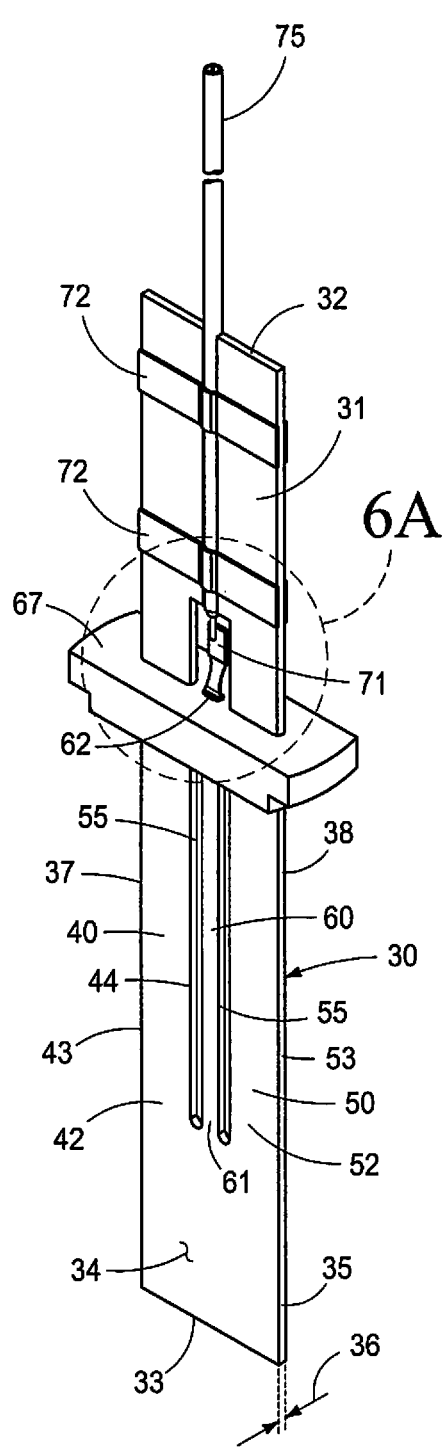
FIG. 6 is an isometric front, side and top view of a first configuration of a probe and support block.
Figure 9:
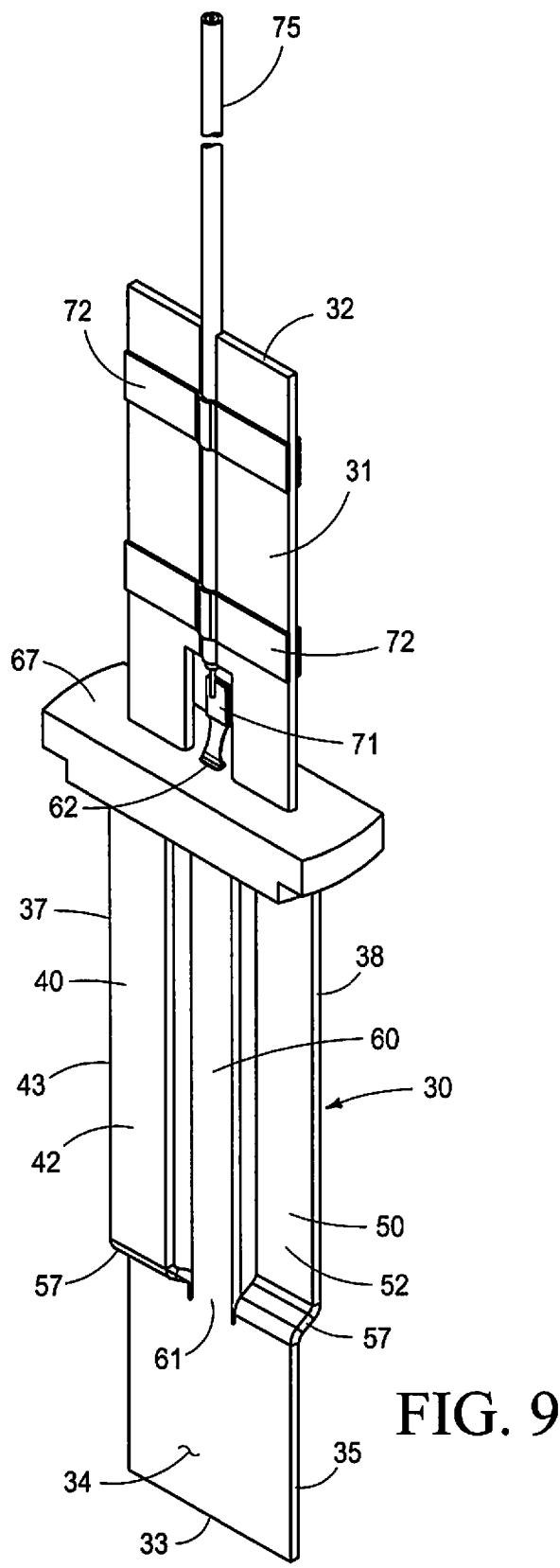
FIG. 9 is an isometric front, side and top view of a second configuration of probe having offset ground plates.
Figure 10:
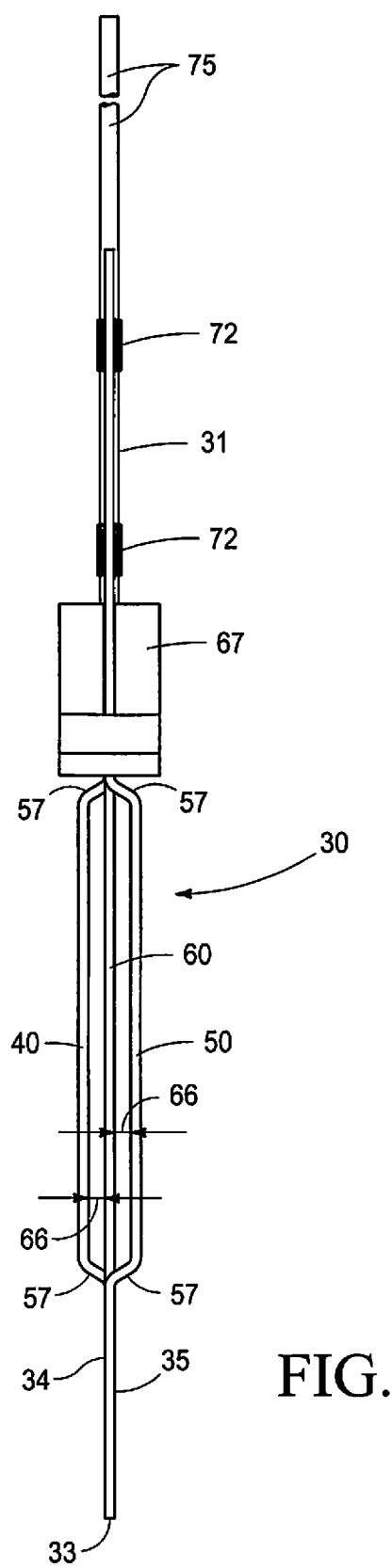
FIG. 10 is an orthographic side view of the second configuration of blade probe of FIG. 9, showing the open structure formed by offsets of the ground plates relative to the center conductor.
Figure 11:
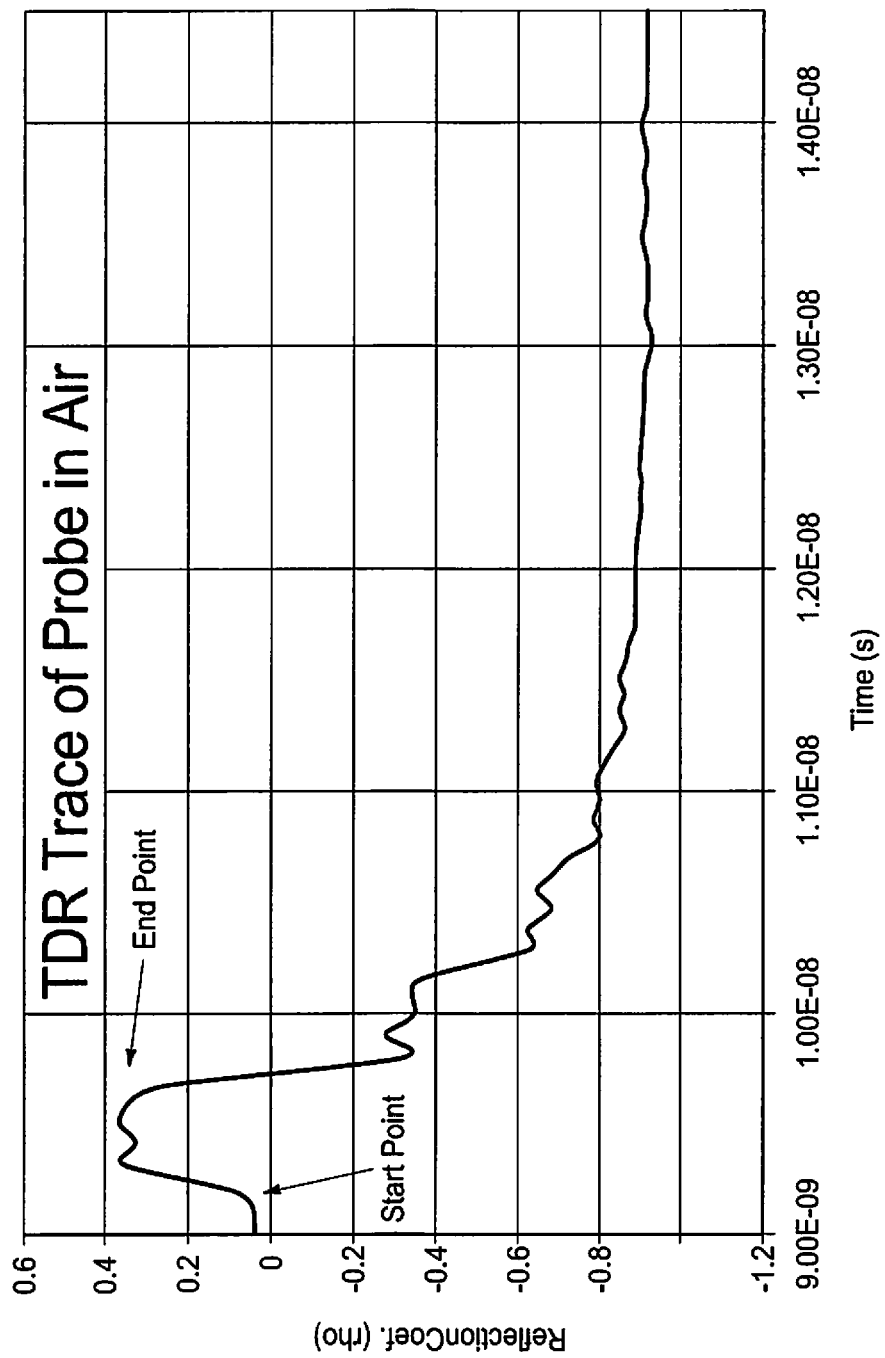
FIG. 11 is a time domain reflectance trace of an electrical pulse through the probe in air showing the start point and the end point.
Figure 12:
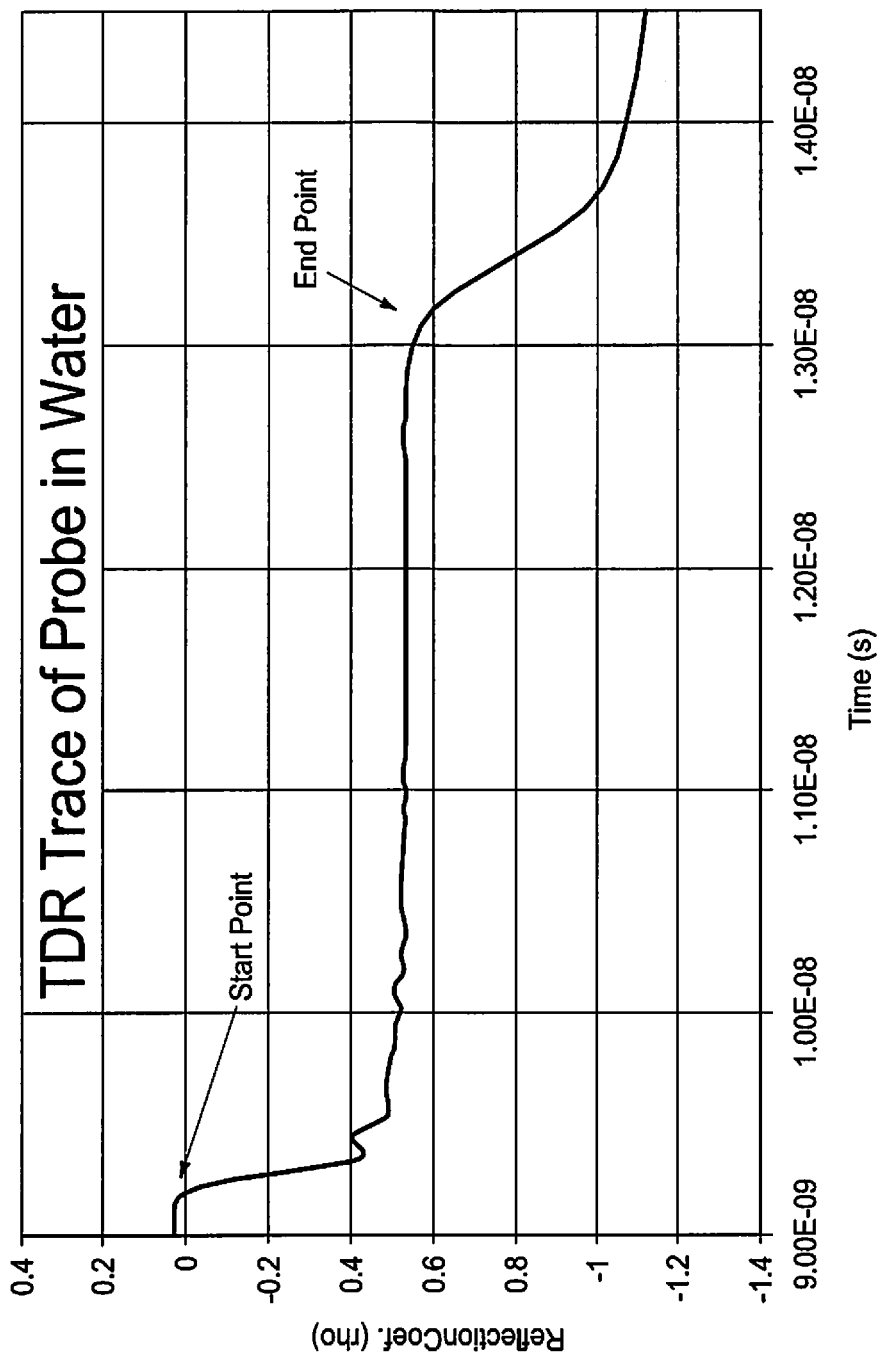
FIG. 12 is a time domain reflectance trace of an electrical pulse through the probe in water showing of the start point and the end point.
Figure 13:
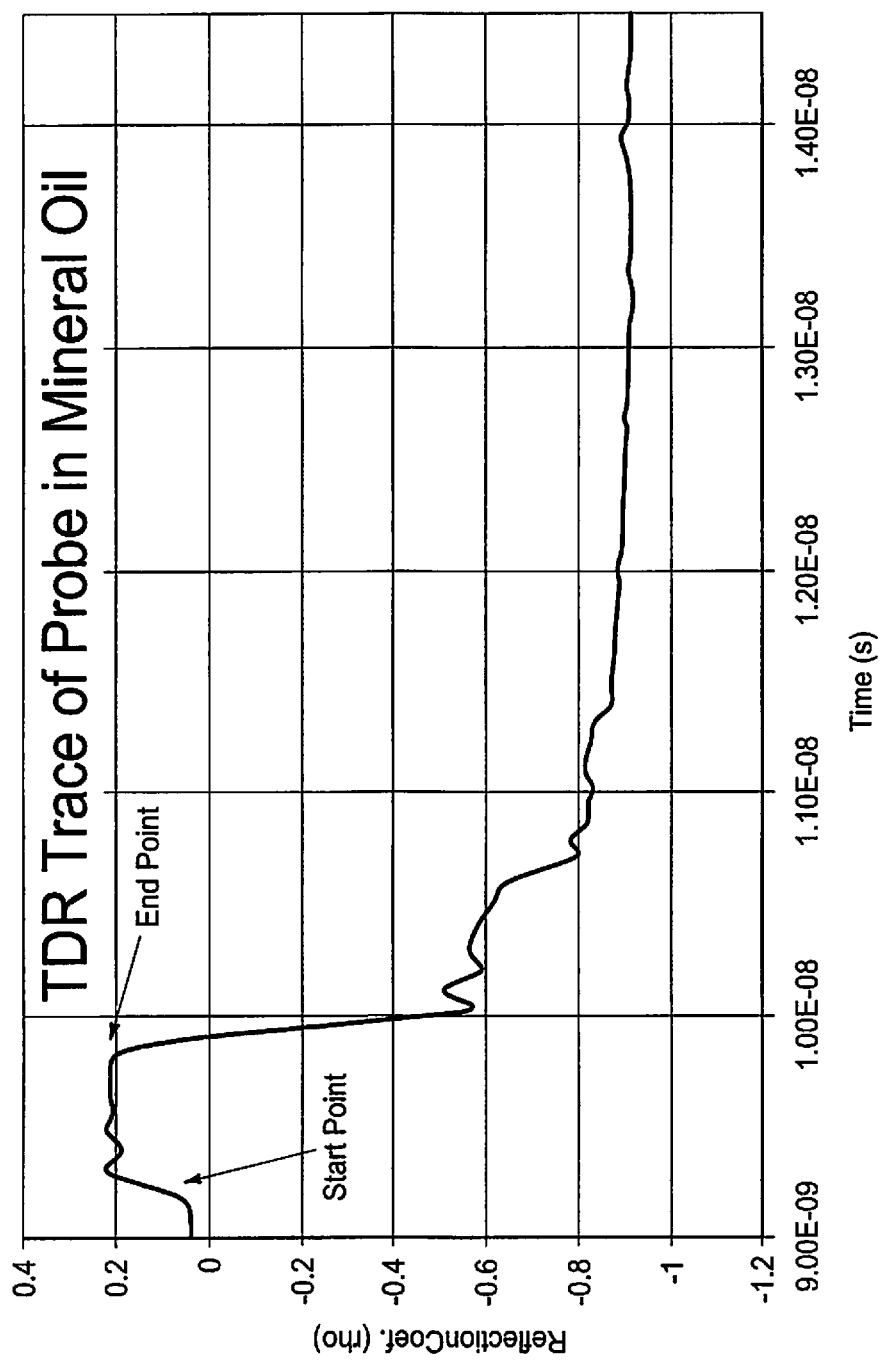
FIG. 13 is a time domain reflectance trace of an electrical pulse through the probe in mineral oil showing the start point and the end point.
Figure 14:
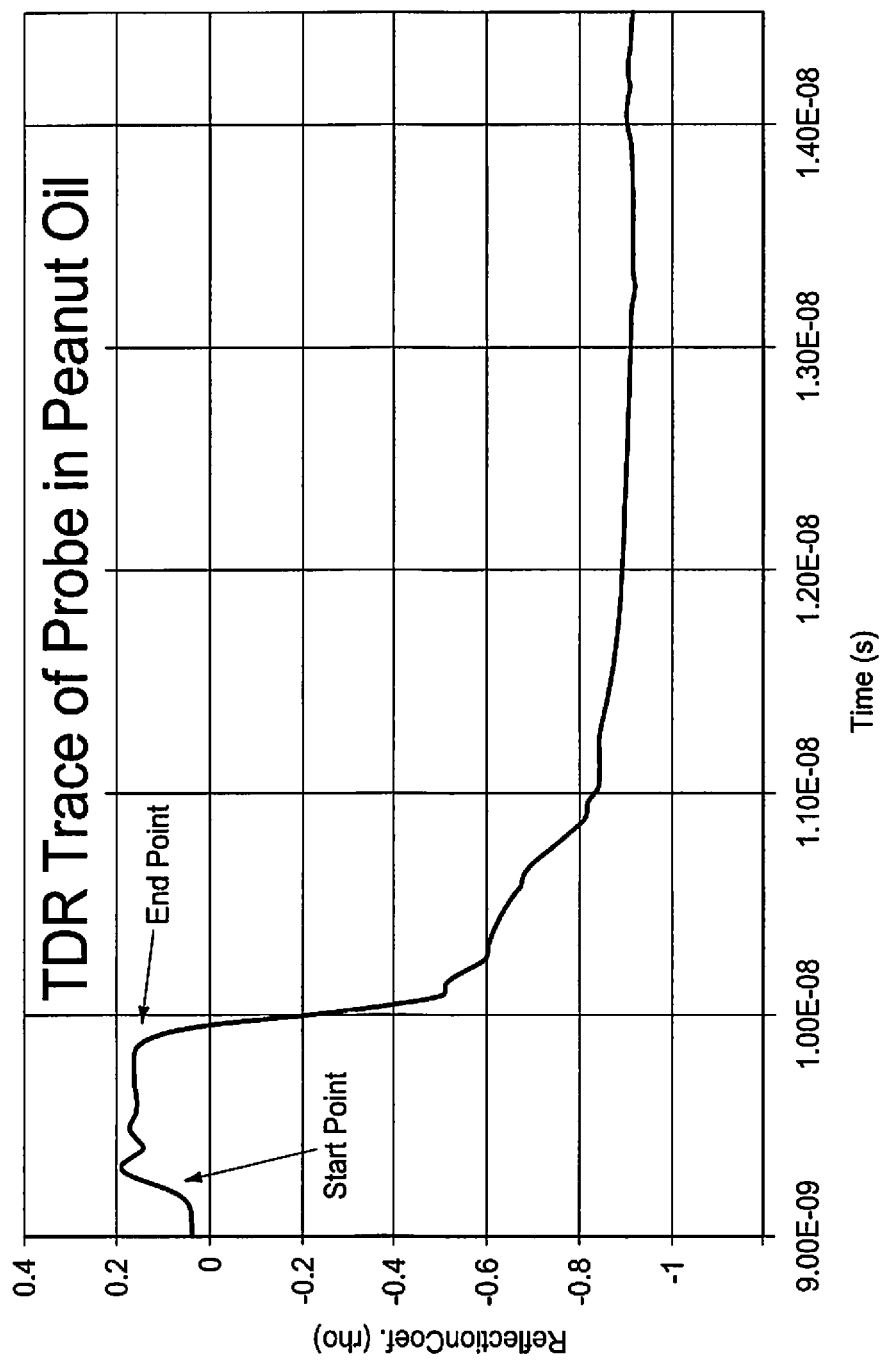
FIG. 14 is a time domain reflectance trace of an electrical pulse through the probe in peanut oil showing the start point and the end point.
Figure 15:
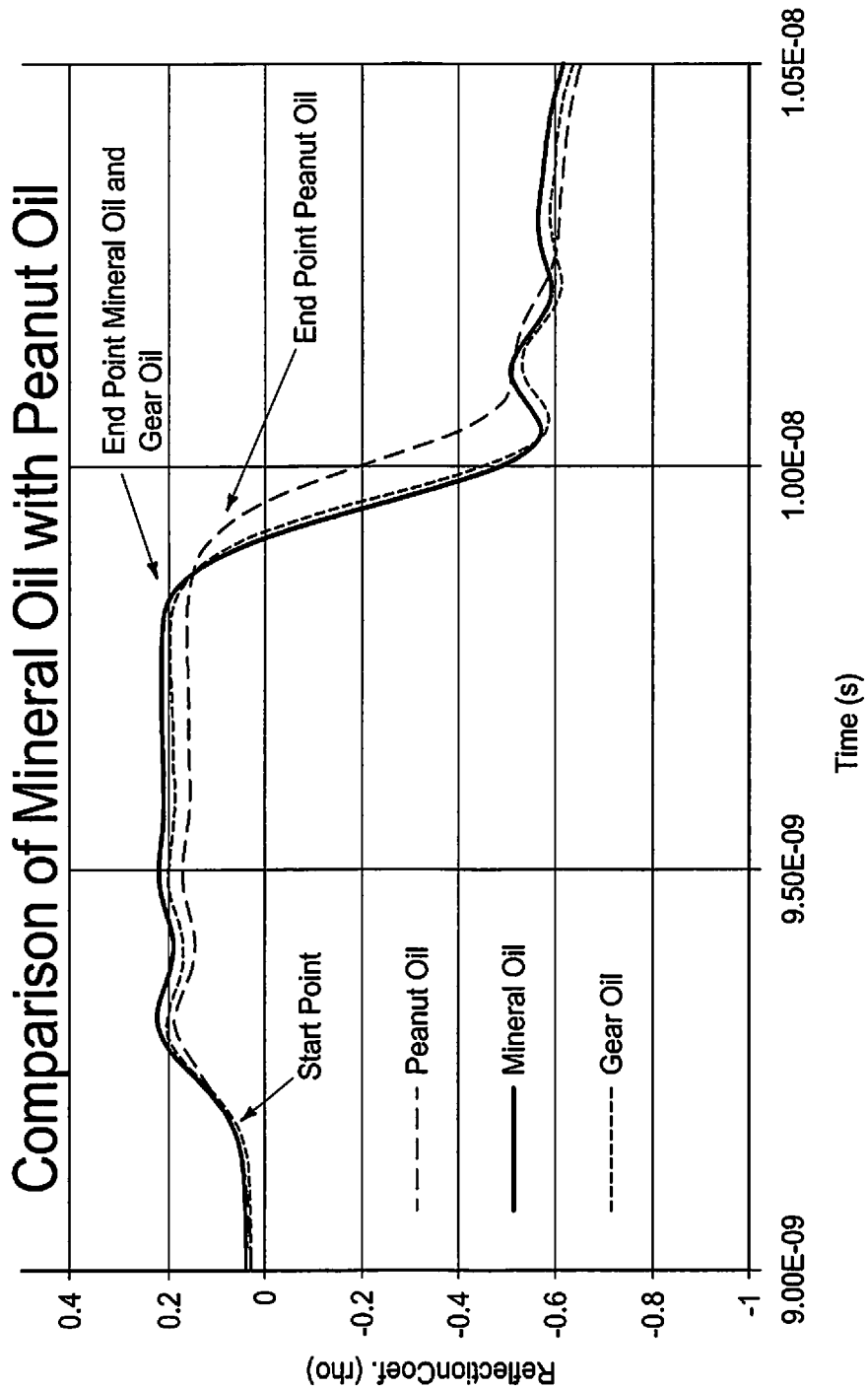
FIG. 15 is a comparison time domain reflectance trace of an electrical pulse through the probe in peanut oil, mineral oil and gear oil showing the start point and the endpoint and showing the similarity in the traces amongst the different types of oils.

As shown in FIGS. 9 and 10, a second design of probe 30 is also contemplated herein. This second probe 30 design is intended to reduce potential (clogging) due to particulates and solids within the fluid 14 moving through the medial channel 28 of the pipe 20 and the grayloc supports 80 and is particularly useful for use in producing wells where the slugs 250 of liquid may contain solids and particulates (not shown), such as, but not limited to sand. In the second contemplated design (FIGS. 9, 10) the first ground plate 40 is offset toward the first surface 34 in the thickness dimension 36 relative to the center conductor 60 defining a gap 55 of approximately 0.080 inches between an inner proximate edge 44 of the first ground plate 40 and the center conductor 60. Similarly, the second ground plate 50 is offset in the thickness dimension 36 toward the second surface 35 by a distance of approximately 0.080 inches to define a gap 55 between the proximate inner edge 54 of the second ground plate 50 and the center conductor 60. The mutual perpendicular and opposite offsetting of the first ground plate 40 and the second ground plate 50 relative to the center conductor 60 is facilitated by bends 57 at a bottom portion of the offset portion (the active length 66), and at an upper portion of the offset portion so that only the active portion 66 of the probe body 31 is laterally offset to allow fluid 14 to flow through the gap 55. (FIG. 10). In other aspects, the second probe design (FIG. 10) is the same as that of the first probe design (FIG. 6).

The first ground plate 40 is offset relative to the elongated center conductor 60 and the generally planar body 31 in a direction opposite the second surface 35 and toward the first surface 34 so as to be spaced apart from the proximate laterally outer edge portion of the elongated center conductor 60 in two mutually perpendicular directions, (in the thickness dimension 36) and the second ground plate 50 is offset relative to the elongated center conductor 60 and the generally planar body 31 in a direction opposite the first surface 34 and toward the second surface 35 so as to be spaced apart from the proximate laterally outer edge portion of the elongated center conductor 60 in two mutually perpendicular directions (in the thickness dimension).

The first ground plate 40 is offset in a thickness dimension toward the first surface 34 and opposite the second surface 35 relative to the center conductor 60 a distance of approximately 0.080 inches, and the second ground plate 50 is offset in a thickness dimension toward the second surface 35, opposite the first surface 34, relative to the center conductor 60 a distance of approximately 0.080 inches. Further, the first surfaces 34 of the first ground plate 40, the elongated center conductor 60 and the second ground plate 60 are parallel to one another but are not coplanar with one another, and the second surfaces 35 of the first ground plate 40, the elongated center conductor 60 and the second ground plate 50 are parallel to one another, but are not coplanar with one another. Further still, the first ground plate 40 and second ground plate 50 are offset from the center conductor 60 a distance of between approximately 0.051 inches and 0.110 inches and a width of the elongated gap 55 between an inner edge of the first ground plate 40 and an inner edge of the second ground 50 plate is about 0.310 inches.

In a third possible configuration (FIGS. 24, 25) the EFP probe 30 is a "through probe" design such that there is no reflection signal generated by a terminal end of the probe 30. Rather, a length of coaxial cable 75 has a first end that is electrically interconnected with the second end 33 of the probe 30 and a second end of the elongated center conductor 60. The coaxial cable 75 has a second opposing end (not shown) that is electrically interconnected with the pulse sampler 150 which effectively creates an "endless loop" which prevents the creation of any terminal-end "reflection signal". The "through probe" configuration (FIGS. 24, 25) has the added benefit of enhancing contrast and lengthening the signal to provide enhanced ability to evaluate the resonance points and permittivity curve of the constituents 15, 16, 17, 17A, 17B, 17C, 17D, 19 surrounding the probe 30.

The third configuration of the probe 30 (FIGS. 24, 25) requires use of a two port TDR (not shown) having one port (not shown) that sends the electrical pulse signal (not shown) (functioning as the pulse emitter 120) and a second (separate) port (not shown) (functioning as the pulse sampler 150) that receives the electrical pulse signal so that any signal confusion is removed, or at least minimized. The dual port system allows determination of phase relationships and the complex permittivity (real and imaginary) curves more efficiently than using the reflected single port system including more subtle variations in the materials being examined.

A complex permittivity curve describes the electrical permittivity of a material and is a property of the material independent of the EFP system and is related to the concept of dielectric constant and the complex permittivity curve for a given material may change with density and temperature.

All materials have electrical permittivity. Oil 15 and water 16 and natural gas 17 and condensates 19 have distinct complex permittivity curves at any density and temperature encountered in extraction operations. A measured complex permittivity curve for an oil-water-gas mixture can be used to determine the oil-water-gas ratio.

Complex permittivity for a mixture can be calculated from scattering parameters of the probe 30 that is submerged in the mixture. The scattering parameters of the probe are a function of the probe 30 geometry and the complex permittivity of the fluid 14 that surrounds it. By knowing the probe 30 geometry and the scattering parameters is sufficient to make an estimate of the complex permittivity of the fluid 14 and its constituents.

The instant method contains a database 172 of known complex permittivity curves for oil 15 and water 16 and natural gas 17 and condensates 19 at ranges of temperatures and pressures.

Scattering parameters are a representation of a passive electrical component, such as an EFP probe 30. A complete set of scattering parameters totally describes the electrical behavior of a component, (the probe 30) and there are different equivalent representations of scattering parameters. One preferred representation is as a time-domain response trace for a unit electric impulse. Another preferred representation is a frequency domain specification of gain and phase shift for inputs at given frequencies.

When represented in the frequency domain, the scattering parameter is a complex number, with the amplitude giving the gain from input to output, and the phase angle of the value matching the phase shift of the output relative to the input.

When the scattering parameters are known, and the input signals are known, the output signals can be calculated by convolving the input signals with the scattering parameters.

With the EFP probe 30, the input pulse signal is known by calibration of the pulse generator 150, and the output is measured. The scattering parameter can then be calculated by de-convolving the input signal from the received signal.

The design of the EFP probe 30 ensures that the scattering parameters of the probe 30 are predictably related to the complex permittivity of the fluid 14 to which the probe 30 is exposed.

Scattering parameters are not properties of the fluid 14, but electrical properties of the EFP probe 30 that can be used to calculate a complex permittivity curve of the fluid 14. Oil 15 and water 16 and natural gas 17 do not have scattering parameters. However, the scattering parameters of the EFP probe 30 are significantly different when submerged in oil 15 or water 16 or natural gas 17.

Like scattering parameters, resonance points are an electrical property of the EFP probe 30. They are not a property of the fluid 14. Oil 15 and water 16 and natural gas 17 and condensates 19 do not have resonance points.

The EFP probe 30 is designed so that its resonance points are significantly different when in oil 15 versus when in water 16 versus when in natural gas 17.

Resonance points are frequencies which resonate with the EFP probe 30. They are near integer or half-integer (1.5, 2.5) multiples of some lowest frequency. The small deviations from one resonance point to the next can be used to estimate the amplitude of the complex permittivity at the frequency of the resonance points.

Resonance points can be determined and measured from an EFP pulse reflected or transmitted signal by analysis of the signal transformed to the frequency domain using an FFT.

Three different techniques are used to calculate dielectric constant and complex permittivity. These techniques can be used with each of the contemplated probe 30 designs.

Each technique is more powerful, but more complicated than the one before. Each can be used simultaneously on the same EFP signal.

The terms Dielectric Constant and Permittivity are related, and to some extent, are the same thing. The dielectric constant is also called the Relative Permittivity. For a material, the relative permittivity is the ratio between the absolute permittivity of the material and the permittivity of free space.

Relative permittivity can be measured by measuring the capacitance between two plates with the material therebetween. The higher the dielectric, the higher the capacitance.

For an AC signal, the permittivity of a material typically varies between frequencies. The dielectric constant, which is only the relative permittivity at 0 Hz and does not say much about the electrical properties of the material at higher frequencies.

Also, with an AC signal, energy can be lost to the material. The combination of a loss-less component and a lossy component of electrical permittivity is represented as a complex number, with the lossy component as the imaginary term.

The speed of the pulse through the probe 30 is inversely related to the dielectric constant of the fluid 14 surrounding the probe 30. As the dielectric constant changes, the time for an electric pulse to leave the EFP and return will also change.

If a sine wave of a single frequency were sent continuously from the EFP to a probe, the wave would reflect from two places: the start of the probe and the end of the probe 30. The reflections would be sine waves of the same frequency.

The reflected sine waves add together and appear as a single sine wave at the EFP. At certain frequencies, the reflecting waves will cancel each other out. This phenomenon is known as destructive interference. At these frequencies, the apparent amplitude of the reflected pulse drops suddenly.

The wavelength of an electric pulse at a given frequency is a function of the speed of the pulse. The speed of the pulse is inversely related to the permittivity at that frequency. From a divisor of a resonance point it is possible calculate the wavelength. From the wavelength and the frequency of the resonance point it is possible to calculate speed, and therefore calculate permittivity.

Because the resonance point technique is a single frequency measurement, the result is frequency dependent permittivity. Because there are multiple resonance points the permittivity is determined at a number of different frequencies.

OPERATION

Having described the method for identifying and characterizing a condensate entrained in a fluid, the operation may be understood.

A source of fluid 13 is provided and is interconnected with a pipe 20 defining the medial channel 28 to provide fluid 14 moving therethrough, the fluid 14 having a volume fraction constituent 15, 16, 17, 17A, 17B, 17C, 17D and condensate 19 that is desired to be identified and characterized and measured, and wherein the volume fraction constituent 15, 16, 17, 17A, 17B, 17C, 17D, 19 has previously calculated and known dielectric constant, and a previously calculated and known resonance points, and wherein information about the previously calculated and known dielectric constant and previously calculated and known resonance points of the volume fraction constituent 15, 16, 17, 19 is stored in, and is accessible from a database 172.

Figure 22:
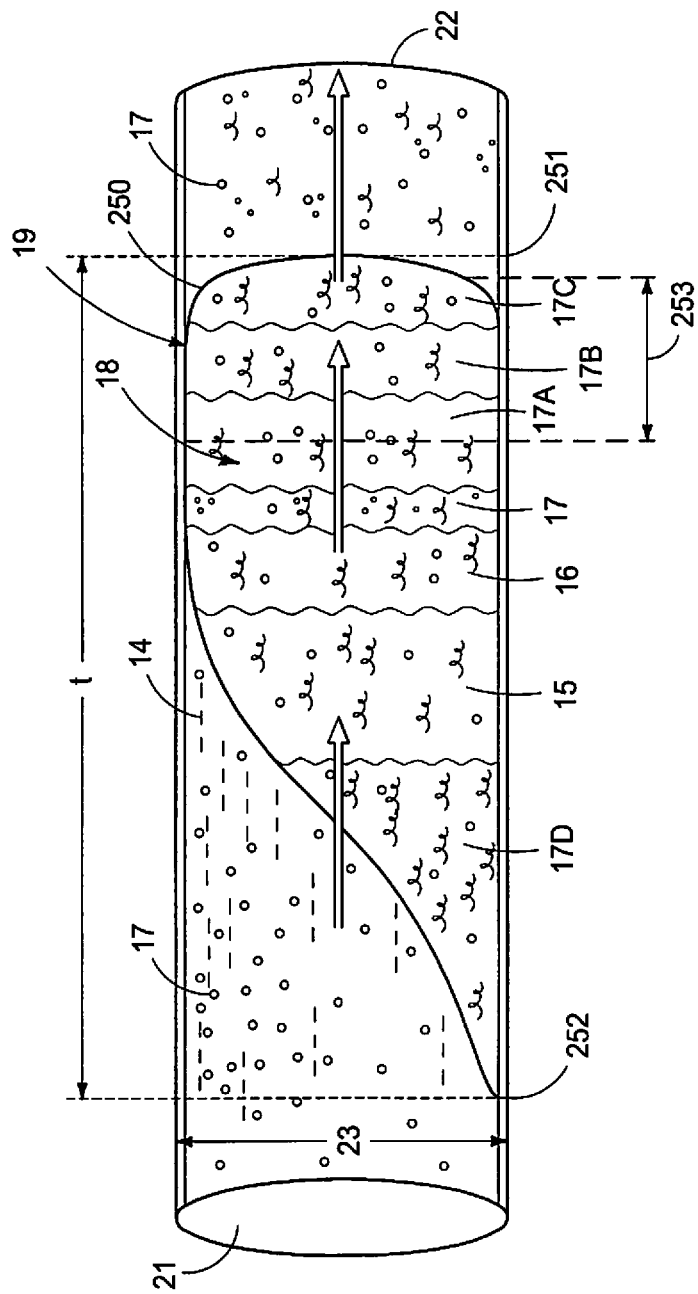
FIG. 22 is an artistic representation of a periodic transient slug of liquid comprised of a variety of condensates passing through a conduit/pipe showing the direction of flow, the leading edge of the slug and the trailing edge of the slug.
Figure 23:
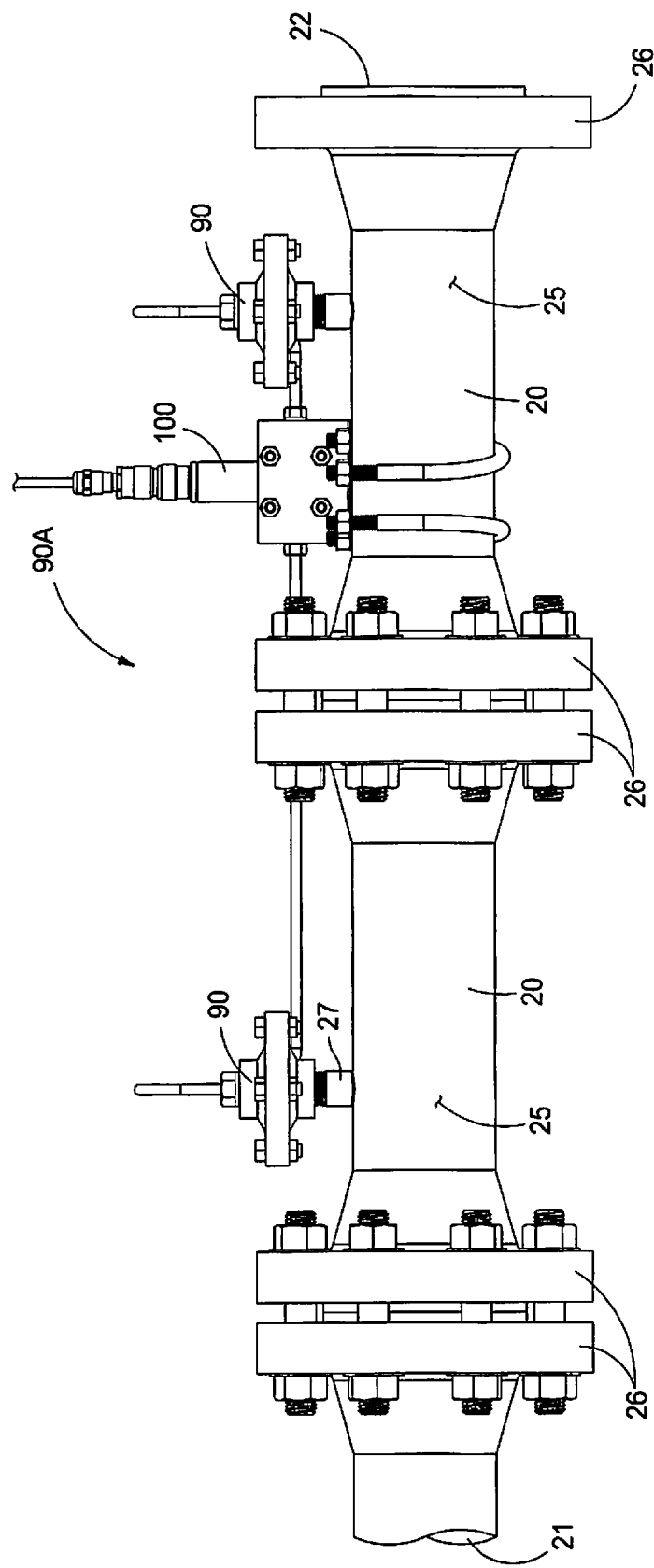
FIG. 23 is an orthographic front to view of a representative optional additional flow meter assembly that may be utilized in the instant inventive method.

The fluid 14 enters the pipe 20 from the source of fluid 13 and passes through the pipe 20 as a liquid slug 250 (See FIG. 22) that may be both transient and periodic. The liquid slug 250 has a leading edge portion 251 and a trailing edge portion 252 and is comprised of a variety of condensate 19 and natural gas 17 such as, but expressly not limited to, ethane 17A, butane 17B, pentane 17C and propane 17D. The condensate 19 and natural gas 17 may further be in the form of an emulsion 18 that is mixed with water 16 and/or oil 15 so that the condensate 19 is entrained within the fluid 14.

The slug 250 is transient in the pipe 20 and commonly has a duration of about two hundred (200) seconds between the leading edge portion 251 and the trailing edge portion 252 when moving through the conduit/pipe 20. The concentration of condensate 19 and volume fraction constituents 17, 17A, 17B, 17C, 17D is typically highest/greatest at or near the leading edge portion 251 of the liquid slug 250 and therefore the measurements/sampling of the constituents of the slug 250 is preferably made at or near the leading edge portion 251 of the slug 250 as the slug passes through the pipe 20 and passed the EFP probes 30A, 30B. The measurements performed by the probes 30A, 30B are performed continuously, including continuously throughout the passage of the liquid slug 250 past the probes 30A, 30B. The most accurate measurements are taken in a period 253 (FIG. 22) that has a duration of approximately two (2) to seven (7) seconds following the leading edge portion 251 of the slug 250. It is proximate the leading edge portion 251 of the slug 250 that the concentrations of the condensates 19 and constituents 17A-D are the highest with the least dissipation by methane gas bubbles. (not shown).

First probe 30A is exposed at least in part to the fluid 14 moving through the pipe 20, the first probe 30A having a known active length, and the first probe 30A is positionally maintained within a medial chamber 85 defined by a grayloc support 80 communicating with the medial channel 28 of the pipe 20, so that the slug 250 and fluid 14 and condensate 19 flows therethrough and thereabout and there-past the first probe 30A.

Second probe 30B is also exposed at least in part to the fluid 14 moving through the pipe 20, a known distance 76 downstream of the first probe 30A, the second probe 30B having an known active length, and the second probe 30B is positionally maintained within a medial chamber 85 defined by a second grayloc support 80A that also communicates with the medial channel 28 of the pipe 20, a known distance 76 downstream of the first grayloc support 80 so that the slug 250, the fluid 14 and the condensate 19 flows therethrough, and thereabout and there-past the second probe 30B.

A back pressure regulator 110 communicating with the medial channel 28 of the pipe 20 may maintain fluid pressure about the probes 30A, 30B at a pressure at least equal to the pressure of the source of the fluid 13 to prevent boiling of the fluid 14 within the pipe 20 to prevent formation of steam within the pipe 20, because steam has a dielectric constant that is similar to the dielectric constant of natural gas 17 and condensate 19 which would make it difficult to distinguish between a volume of natural gas 17 and condensate 19 and a volume of steam.

A first electrical pulse emitter 120 electronically generates an electrical pulse which is conveyed to the first probe 30A through the coaxial cable 75. The electrical pulse then generates an electrical pulse reflection upon interacting with a changed electrical impedance (which is indicated as an end of the first probe 30A) and which is caused by a change in sensed dielectric constant of the volume fraction constituent 15, 16, 17, 19 to which the first probe 30A is exposed. The first electrical pulse sampler 150 receives and senses of the electrical pulse reflection.

Similarly, the second electrical pulse emitter 120 electronically generates an electrical pulse which is conveyed to the second probe 30B through the coaxial cable 75. The electrical pulse similarly generates an electrical pulse reflection upon interacting with the changed electrical impedance (which is indicated as an end of the second probe 30B) and which is caused by a change in sensed dielectric constant of the volume fraction constituent 15, 16, 17, 19 to which the second probe 30B is exposed. The second electrical pulse sampler 150 receives and senses of the electrical pulse reflection.

If the third contemplated configuration of probe 30 (FIGS. 24, 25) is utilized for the first probe 30A and the second probe 30B, the change in electrical impedance of the fluid 14 is detected as a reflection signal that is electrically communicated to the interconnected pulse sampler 150. A portion of the original electrical pulse signal (not shown) communicates through the entire active length of the probe 30 and thereafter to the interconnected pulse sampler 150 via the coaxial cable 75. The difference is distance traveled (measured as a time delay) by the electrical pulse reflection signal (due to the change in impedance of the fluid 14/condensate 19) and the electrical pulse pass through signal enhances the signal contrast.

The computer 170 is electronically coupled with the first probe 30A, the first electrical pulse emitter 120, the first electrical pulse sampler 150 and the database 172. The computer 170 determines a time delay between the electrical pulse emission into the first probe 30A and receipt of the sensed electrical pulse reflection from the first probe 30A.

The computer 170 is also electronically coupled with the second probe 30B, the second electrical pulse emitter 120, the second electrical pulse sampler 150 and the database 172. The computer 170 also determines a time delay between the electrical pulse emission into the second probe 30B and receipt of the sensed electrical pulse reflection from the second probe 30B.

The computer 170 performs the time domain evaluation by correlating and comparing the determined time delay between pulse emission and pulse reflection receipt to the information within the database 172 to match the determined time delay to similar time delays generated by known dielectric constants, and then the computer 170 correlates the identified dielectric constant to known and previously determined volume fraction constituents 15, 16, 17, 19 having such dielectric constants. The computer also performs the frequency domain evaluation by determining/calculating the resonance points of the volume fraction constituents 15, 16, 17 and condensate 19 and concentrations thereof in the fluid 14 by applying a Fast Fourier Transform (FFT) to the previously determined time delay. A Power Spectral Density (PSD) evaluation is then made of the calculated resonance points by the computer 170 to determine the average power, amplitude and frequency of the volume fraction constituents 15, 16, 17 and condensate 19. The computer 170 then correlates the resonance points resulting from the FFT and PSD to the previously calculated and known resonance points as provided in the database 172 as a second measure to identify the volume fraction constituents 15, 16, 17 and condensates 19 entrained in the fluid 14 and to measure the volume of the volume fraction constituents 15, 16, 17 and condensate 19 in the fluid 14. The resonance points may also be correlated with the known permittivity curves stored in the database 172 so as to identify the volume fraction constituents 15, 16, 17 and condensates 19 entrained in the fluid 14 and to measure the volume of the volume fraction constituents 15, 16, 17 and condensate 19 in the fluid 14.

A first output (not shown) is generated by the first probe 30A when a volume fraction constituent 15, 16, 17 and condensate 19 is sensed by the first probe 30A, and a second output (not shown) is generated by the second probe 30B when the same volume fraction constituent 15, 16, 17 and condensate 19 is subsequently sensed by the second probe 30B. The first and second probe outputs (not shown) are communicated to the computer 170 through the coaxial cable 75 wherein the computer 170 uses the time delay between the first probe 30A output and the second probe 30B output to determine the velocity of the volume fraction constituents 15, 16, 17 and condensate 19 moving through the conduit or pipe 20. The externally mounted auxiliary fluid flow measurement device 90A communicating with the pipe 20 downstream of the second probe 30B and electrically communicating with the computer 170 may provide additional, and independent, volumetric flow data to more accurately determine and measure volumes of the fluid 14 and constituents and condensate 19.

Display 171 is electronically coupled with the computer 170 and receives the identification of the volume fraction constituents 15, 16, 17, 17A, 17B, 17C, 17D and condensate 19 and the volume fraction 15, 16, 17 volume calculation data from the computer 170 to generate a user perceivable output (not shown) which identifies the volume fraction constituents 15, 16, 17 and condensate 19 entrained in the fluid 14 and the volume thereof moving through the pipe 20 continuously and in real time.

The instant invention also provides a method for identifying and characterizing the volume fraction constituents 15, 16, 17 of a fluid 14 and condensates 19 entrained therein. The method is first initiated by providing a source of fluid 13 which communicates with the pipe 20 that defines a medial channel 28 for the fluid 14 to move therethrough. The fluid 14 has a volume fraction constituent 15, 16, 17 and condensate 19 and each volume fraction constituent 15, 16, 17 and condensate 19 has a previously calculated and known dielectric constant and previously calculated and known resonance points.

The database 172, which is assessable by the computer 170, has stored assessable information about the previously calculated and known dielectric constant of each volume fraction constituent 15, 16, 17 and condensate 19 and stored assessable information about the previously calculated and known resonance points of each volume fraction constituent 15, 16, 17 and condensate 19, and each volume fraction constituent at various concentrations.

The first probe 30A is positionally maintained within the upstream grayloc support 80, and the first probe 30A is exposed, at least in part, to the fluid 14 moving through the medial channel 28 of the pipe 20 and through the upstream grayloc support 80. The second probe 30B is similarly positionally maintained within a second grayloc support 80A, and the second probe 30B is exposed, at least in part, to the fluid 14 moving through the medial channel 28 of the pipe 20 and through the second grayloc support 80A downstream a known distance 76 from the first probe 30A.

The back pressure regulator 110 which communicates with the medial channel 28 of the pipe 20 maintains fluid pressure within the medical channel 28 and about the first and second probes 30A, 30B respectively, at a pressure at least equal to the pressure of the source of fluid 13 to prevent boiling of the fluid 14 within the medial channel 28 of the pipe 20.

The first electrical pulse emitter 120 electronically generates an electrical pulse that is conveyed to the first probe 30A through the coaxial cable 75. The electrical pulse is conveyed into the first probe 30A and generates an electrical pulse reflection when the electrical pulse travels the entire active length of the first probe 30A, or earlier interacts with a changed electrical impedance or a changed dielectric constant of a volume fraction constituent 15, 16, 17 and/or condensate 19 to which the first probe 30A is at least partially exposed. The pulse reflection is received by the first electrical pulse sampler 150 that is electronically coupled with the first probe 30A by the coaxial cable 75.

Similarly, the second electrical pulse emitter 120 electronically generates an electrical pulse that is conveyed to the second probe 30B through the coaxial cable 75. The electrical pulse is conveyed into the second probe 30B and a generates an electrical pulse reflection when the electrical pulse travels the entire active length of the second probe 30B or earlier interacts with a changed electrical impedance or a changed dielectric constant of a volume fraction constituent 15, 16, 17 and/or condensate 19 to which the second probe 30B is at least partially exposed. The pulse reflection is received by a second electrical pulse sampler 150 that is electronically coupled with the second probe 30B by the coaxial cable 75.

The computer 170 is electronically coupled with the probes 30A, 30B the electrical pulse emitters 120, the electrical pulse samplers 150 and the database 172.

The computer 170 determines a time delay between the electrical pulse emission into each probe 30A, 30B and receipt of the electrical pulse reflections from each probe 30A, 30B.

The computer 170 correlates the determined time delay between the electrical pulse emission into each probe 30A, 30B, and receipt of the electrical pulse reflection from the respective probe 30A, 30B to the information stored within the database 172 of known time delays generated by known dielectric constants of known volume fraction constituents 15, 16, 17 and condensate 19 to provide a measure to identify the volume fraction constituents 15, 16, 17 and condensate 19 entrained within the fluid 14.

The computer 170 applies a Fast Fourier Transform (FFT) to the determined time delay to generate a sine wave frequency based upon the determined time delay. The computer 170 also calculates the Power Spectral Density (PSD) of the generated sine wave frequency to determine the average power, amplitude and frequency of the sine wave to identify resonance points. The computer 170 correlates the frequency from the Fast Fourier Transform (FFT) and the resonance points of the PSD to the database 172 of known resonance points of known volume fraction constituents 15, 16, 17 and condensate 19 to provide another measure to identify the volume fraction constituents 15, 16, 17 and condensate 19 within the fluid 14 and also to measure the volume of the volume fraction constituents 15, 16, 17 and condensate 19 entrained in the fluid 14.

A first output (not shown) is generated by the first probe 30A when a volume fraction constituent 15, 16, 17 and condensate 19 is sensed by the first probe 30A and identified by the computer 170, and a second output (not shown) is generated by the second probe 30B when the same volume fraction constituent 15, 16, 17 and condensate 19 is subsequently sensed by the second probe 30B and identified by the computer 170.

The volume of each volume fraction constituent 15, 16, 17 and condensate 19 moving through the pipe 20 is calculated by using the determined time delay between the first probe 30A output and the second probe 30B output by calculating the velocity of the sensed volume fraction constituent 15, 16, 17 and condensate 19 moving the known distance 76 and using the known interior diameter 23 of the pipe 20.

Display 171 which is electronically coupled with the computer 170 and which receives the identification of the volume fraction constituent 15, 16, 17 and condensate 19, and the first probe 30A output (not shown) and the second probe 30B output (not shown) and the correlation of resonance points of the volume fraction constituents 15, 16, 17 and condensate 19 generates a user perceivable output (not shown) which identifies each volume fraction constituent 15, 16, 17 and condensate 19 entrained in the fluid 14, and the volume thereof moving through the pipe 20 on a real-time and continuous basis.

A method for identifying, and characterizing a periodic release of a given condensate which is entrained within a source of a fluid, comprising: providing a source of a fluid 13 having a given composition which includes a major volume fraction constituent, and wherein at least one condensate 19 is periodically released, and is then entrained within the source of the fluid 13, and wherein the major volume fraction constituent, and the at least one condensate 19 each have a previously determined, and known, dielectric constant, and/or a previously determined, and known, resonance point; providing a database 172 having accessible, and stored information about the previously determined, and known dielectric constants of the major volume fraction constituent, and/or the at least one condensate 19, and accessible and stored information about the previously determined, and known resonance points of given concentrations of the major volume fraction, constituent and/or the at least one condensate 19; providing a probe 30 which is exposed, at least in part, to the source of fluid 14, and which further has a known length dimension; providing an electrical pulse emitter 120 which, when energized, generates a given electrical pulse which is electrically delivered to the probe 30, and wherein the electrical pulse electrically travels along the known length dimension of the probe 30, and further generates an electrical pulse reflection; providing an electrical pulse sampling device 150 which is electrically coupled in electrical pulse receiving, and sensing relation relative to the probe 30; providing a computer 170 which is electrically coupled with the probe 30, the electrical pulse emitter 120, the electrical pulse sampling device 150, the database 172, and the display 171, and wherein the computer 170 determines a time period which elapses between the electrical pulse emission sent into the probe 30, and the receipt of the sensed electrical pulse reflection received from the probe 30, and wherein the resonance point of the major volume fraction constituent, and/or the resonance point of the at least one condensate 19 are individually calculated by the computer 170 from the determined time periods, and/or the computer 170 correlates the determined time period to the previously determined, and known, dielectric constants, and wherein the computer 170 then correlates the calculated resonance points of the major volume fraction constituent, and/or the at least one condensate 19, as provided in the database 172, so as to identify a characteristic of the major volume fraction constituent, and the at least one condensate 19 which is entrained within the source of fluid 14; and providing a user interface which is electronically coupled with the computer 170, and which further generates a user perceivable output which identifies the at least one characteristic of the major volume fraction constituent, and the at least one condensate 19, respectively.

A method wherein the condensate 19 which is entrained within the source of the fluid 14 is transiently, and periodically released, and wherein the method further comprises the step of measuring the transient and periodic release of the fluid 14 and condensate 19 over a given time period 253.

A method wherein the transient, and periodic release of the condensate 19, and which further is entrained with the source of the fluid 14, takes place over a time period of less than about 200 seconds.

A method further comprising electrically sampling the source of the fluid 14 having the given composition, and which further includes the major volume fraction constituent, and the at least one condensate 19, during a time period 253 of less than about 7 seconds after the beginning 251 of the given transient, and periodic release of the fluid 14 entraining the condensate 19.

A method further comprising electrically sampling the source of the fluid 13 having the given composition, and which includes the major volume fraction constituent, and the at least one condensate 19, during a time period 253 when the major volume fraction constituent, which includes the at least one condensate 19, has the least concentration of a source of methane gas.

A method wherein the periodic and transient release of the fluid 14 entraining the condensate 19 has a leading edge 251, and further contains water 16, and at least one hydrocarbon 17, each having a predetermined and known resonance point and a predetermined and known dielectric constant, and wherein the method further comprises measuring the volume fraction of the water 16, and the volume fraction of the at least one hydrocarbon 17 in the periodic and transient release of the fluid 14 entraining the condensate 19 near the leading edge 251 thereof, by employing electric field perturbation which is based, at least in part, upon a time domain methodology.

A method further comprising providing an elongated conduit 20 having an internal bore 28 which has a predetermined, substantially uniform, inside diametral dimension 23; providing two electric field perturbation probes 30A, 30B, and positioning each of the electric field perturbation probes 30A, 30B, at least in part, within the bore 28 of the elongated conduit 20, and at a known, and predetermined distance 76, one relative to the other; providing a fluid pressure sensor which is mounted in a fluid pressure sensing relationship relative to the internal bore 28 of the elongated conduit 20, and which further generates a fluid pressure signal; providing a temperature sensor 100 which is mounted in temperature sensing relation relative to the internal bore 28 of the elongated conduit 20, and which further generates fluid temperature signal; electrically coupling the two electric field perturbation probes 30A, 30B, fluid pressure sensor, and temperature sensor 100 in a signal transmitting relationship relative to the computer 170; delivering the source of the fluid 13 which includes the major volume fraction constituent, and the at least one condensate 19, into the internal bore 28 of the elongated conduit 20; electrically sampling, with the computer 170, each of the respective two electric field perturbation probes 30A, 30B, fluid pressure, and/or temperature sensor 100 signals; and correlating the signals received from the at least two electric field perturbation probes 30A, 30B, the pressure sensor and/or temperature sensor 100, with the computer 170, so as to provide a characterization of the source of the fluid 13.

A method wherein each of the electric perturbation sensors 30A, 30B are located at predetermined, spaced apart, sensing stations 80 which are located along the elongated conduit 20; and electrically sampling with the computer 170, at each of the sensing stations 80, at a speed of about 500 frames per second.

A method further comprising calculating, with the computer 170, a flow velocity of the source of the fluid 13 through the internal bore 28 of the elongated conduit 20 from the signals received from the two electric field perturbation probes 30A, 30B, and the temperature 100 and fluid pressure sensors.

A method further comprising characterizing, with the computer 170, the average composition of the source of the fluid 13 in the region of the respective, spaced 76, sensing stations 80 by utilizing the signals received from the respective, electric field perturbation sensors 30A, 30B; and estimating, by utilizing the computer 170, a total flow volume of the source of the fluid 13, and a fractional volume of the at least one hydrocarbon 17 which is entrained with the source of the fluid 14.

A method further comprising calculating, with the computer 170, an approximate fluid density of the source of the fluid 13, by utilizing the signals received from the temperature 100 and pressure sensors, during a given sampling time; and providing an auxiliary, and externally mounted fluid flow measurement device 90A and coupling the auxiliary, and externally mounted fluid flow measurement device 90A in a signal transmitting relationship relative to the computer 170; delivering the source of fluid 13 to the auxiliary, and externally mounted, fluid flow measurement device 90A, and generating a signal with the auxiliary and externally mounted fluid flow measurement device 90A which is transmitted to the computer 170; measuring the fluid 14 flowing movement of the source of the fluid 13 through the auxiliary, and externally mounted, fluid flow measurement device 90A; estimating the total flow of the source of fluid 13, with the computer 170, by utilizing the signal generated by the auxiliary, and externally mounted, fluid flow measurement device 90A; and improving the estimated calculation of the total flow volume of the source of the fluid 13, and the fractional volume of the at least one hydrocarbon 17 which is entrained with the source of the fluid 14, by utilizing the estimated total flow of the source of fluid, and which is detected by the auxiliary, and externally mounted fluid flow measuring device 90A, by employing the computer 170.

A method further comprising applying a Fourier Transform calculation to the sensed electrical pulse reflection received from the probe 30, and which is used to determine a resonant frequency and resonance point of at least one of the volume fraction constituents 17.

A method further comprising applying a Power Spectral Density (PSD) calculation, by means of the computer 170, to the Fourier Transform (FFT) frequency so as to determine an amplitude, and strength of at least one of the given resonance points.

A method wherein the volume fraction constituent 17 is a multiplicity of volume fraction constituents.

A method wherein the multiplicity of volume fraction constituents 17 includes a liquid and a gas.

A method for identifying and characterizing a transient and periodic condensate 19 entrained in a fluid 14 comprising determining a dielectric constant of a condensate 19 moving through a pipe 20 by determining a time delay between an electrical pulse emission into a probe 30 exposed, at least in part, to the fluid 14 and a reflection of the electrical pulse emission from the probe 30; correlating the determined time delay to a database 172 of known dielectric constants of known condensates 19 to identify the condensate 19; applying a Fourier Transform to the determined time delay to generate frequency resonance points of the condensate 19; correlating the generated resonance points of the condensate 19 to a database 172 of known resonance points of known condensates 19 and known concentrations of condensates 19 to identify the condensate 19; and providing a user interface which generates a user perceivable output which identifies the condensate 19 in the fluid 14 in a user perceivable form.

A method further comprising providing a pipe 20 having a known interior diameter 23 that communicates with the source of the fluid 13 so that a volume of the fluid 14 moves through the pipe 20 at a velocity; providing a second probe 30B exposed at least in part to the fluid 14 moving through the pipe 20 a known distance 76 downstream from the first probe 30A; generating a first output by the first probe 30A when a condensate 19 is sensed by the first probe 30A and generating a second output by the second probe 30B when the same condensate 19 is sensed by the second probe 30B, and communicating the first and second probe outputs to the computer 170; determining a volume of the condensate 19 moving through the pipe 20 by unit of time by calculating a time difference between the first probe 30A output and the second probe 30B output to determine the velocity of the fluid 14 moving through the pipe 20; and correlating the determined resonance points of the condensate 19 with the database 172 of known resonance points of concentrations of condensates to determine the volume of the condensate 19 moving through the pipe 20.

A method further comprising calculating a permittivity of the at least one condensate 19 with the computer 170, by utilizing the calculated resonance points of the at least one condensate 19, and utilizing the known and predetermined information stored in the database 172, to identify the at least one condensate 19.

The instant inventive method is also usable with a probe 30 that is a through probe.

We claim:

1. A method for identifying, and characterizing a periodic release of a given condensate which is entrained within a source of a fluid, comprising:
   providing a source of a fluid having a given composition which includes a major volume fraction constituent, and wherein at least one condensate is periodically released, and is then entrained within the source of the fluid, and wherein the major volume fraction constituent, and the at least one condensate each have a previously determined, and known, dielectric constant, and/or a previously determined, and known, resonance point;
   providing a database having accessible, and stored information about the previously determined, and known dielectric constants of the major volume fraction constituent, and/or the at least one condensate, and accessible and stored information about the previously determined, and known resonance points of given concentrations of the major volume fraction, constituent and/or the at least one condensate;
   providing a probe which is exposed, at least in part, to the source of fluid, and which further has a known length dimension;
   providing an electrical pulse emitter which, when energized, generates a given electrical pulse which is electrically delivered to the probe, and wherein the electrical pulse electrically travels along the known length dimension of the probe, and further generates an electrical pulse reflection;
   providing an electrical pulse sampling device which is electrically coupled in electrical pulse receiving, and sensing relation relative to the probe;
   providing a computer which is electrically coupled with the probe, the electrical pulse emitter, the electrical pulse sampling device, and the database, and wherein the computer determines a time period which elapses between an electrical pulse emission sent into the probe, and receipt of a sensed electrical pulse reflection received from the probe, and wherein the previously determined and known resonance point of the major volume fraction constituent, and/or the previously determined and known resonance point of the at least one condensate are individually calculated by the computer from the determined time periods, and/or the computer correlates the determined time period to the previously determined, and known, dielectric constants, and wherein the computer then correlates the calculated resonance points of the major volume fraction constituent, and/or the at least one condensate, as provided in the database, so as to identify a characteristic of the major volume fraction constituent, and the at least one condensate which is entrained within the source of fluid; and
   providing a user interface which is electronically coupled with the computer, and which further generates a user perceivable output which identifies the at least one characteristic of the major volume fraction constituent, and the at least one condensate, respectively.

2. A method as claimed in claim 1, and wherein the condensate which is entrained within the source of the fluid is transiently, and periodically released, and wherein the method further comprises the step of measuring transient and periodic releases of the condensate entrained in the source of the fluid over a given time period.

3. A method as claimed in claim 2, and wherein the transient, and periodic release of the condensate, and which further is entrained with the source of the fluid, takes place over a time period of less than about 200 seconds.

4. A method as claimed in claim 3, and wherein the method further comprises:
   electrically sampling the source of the fluid having the given composition, and which further includes the major volume fraction constituent, and the at least one condensate, during a time period of less than about 7 seconds after beginning of the transient, and periodic release of the fluid entraining the condensate.

5. A method as claimed in claim 3, and wherein the method further comprises:
   electrically sampling the source of the fluid having the given composition, and which includes the major volume fraction constituent, and the at least one condensate, during a time period when the major volume fraction constituent, which includes the at least one condensate, has the least concentration of a source of methane gas.

6. A method as claimed in claim 5, and wherein the periodic and transient release of the fluid entraining the condensate has a leading edge, and further contains water, and at least one hydrocarbon, each having a predetermined and known resonance point and a predetermined and known dielectric constant, and wherein the method further comprises measuring the volume fraction of the water, and the volume fraction of the at least one hydrocarbon in the periodic and transient release of the fluid entraining the condensate near the leading edge thereof, by employing electric field perturbation which is based, at least in part, upon a time domain methodology.

7. A method as claimed in claim 6, and further comprising:

providing an elongated conduit having an internal bore which has a predetermined, substantially uniform, inside diametral dimension;

providing two electric field perturbation probes, and positioning each of the electric field perturbation probes, at least in part, within the bore of the elongated conduit, and at a known, and predetermined distance, one relative to the other;

providing a fluid pressure sensor which is mounted in a fluid pressure sensing relationship relative to the internal bore of the elongated conduit, and which further generates a fluid pressure signal;

providing a temperature sensor which is mounted in temperature sensing relation relative to the internal bore of the elongated conduit, and which further generates fluid temperature signal;

electrically coupling the two electric field perturbation probes, fluid pressure sensor, and temperature sensor in a signal transmitting relationship relative to the computer;

delivering the source of the fluid which includes the major volume fraction constituent, and the at least one condensate, into the internal bore of the elongated conduit;

electrically sampling, with the computer, each of the respective two electric field perturbation probes, fluid pressure, and/or temperature sensor signals; and correlating the signals received from the at least two electric field perturbation probes, the pressure sensor and/or temperature sensor, with the computer, so as to provide a characterization of the source of the fluid.

8. A method as claimed in claim 7, and wherein each of the electric perturbation sensors are located at predetermined, spaced apart, sensing stations which are located along the elongated conduit; and electrically sampling with the computer, at each of the sensing stations, at a speed of about 500 frames per second.

9. A method as claimed in 8, and further comprising:

calculating, with the computer, a flow velocity of the source of the fluid through the internal bore of the elongated conduit from the signals received from the two electric field perturbation probes, and the temperature and fluid pressure sensors.

10. A method as claimed in 9, and further comprising:

characterizing, with the computer, the average composition of the source of the fluid in the region of the respective, spaced, sensing stations by utilizing the signals received from the respective, electric field perturbation sensors; and estimating, by utilizing the computer, a total flow volume of the source of the fluid, and a fractional volume of the at least one hydrocarbon which is entrained with the source of the fluid.

11. A method as claimed in claim 10, and further comprising:

calculating, with the computer, an approximate fluid density of the source of the fluid, by utilizing the signals received from the temperature and pressure sensors, during a given sampling time; and providing an auxiliary, and externally mounted fluid flow measurement device and coupling the auxiliary, and externally mounted fluid flow measurement device in a signal transmitting relationship relative to the computer;

delivering the source of fluid to the auxiliary, and externally mounted, fluid flow measurement device, and generating a signal with the auxiliary and externally mounted fluid flow measurement device which is transmitted to the computer;

measuring the fluid flowing movement of the source of the fluid through the auxiliary, and externally mounted, fluid flow measurement device;

estimating the total flow of the source of fluid, with the computer, by utilizing the signal generated by the auxiliary, and externally mounted, fluid flow measurement device; and improving the estimated calculation of the total flow volume of the source of the fluid, and the fractional volume of the at least one hydrocarbon which is entrained with the source of the fluid, by utilizing the estimated total flow of the source of fluid, and which is detected by the auxiliary, and externally mounted fluid flow measuring device, by employing the computer.

12. A method as claimed in claim 1, and further comprising:

applying a Fast Fourier Transform calculation to the time period which elapses between the electrical pulse emission sent into the probe, and receipt of the electrical pulse reflection received from the probe, and which is used to determine a resonant frequency and resonance point of at least one of the volume fraction constituents.

13. A method as claimed in claim 12, and further comprising:

applying a Power Spectral Density (PSD) calculation, by means of the computer, to the Fast Fourier Transform (FFT) frequency so as to determine an amplitude, and strength of at least one of the previously determined and known resonance points.

14. A method as claimed 13, and wherein the volume fraction constituent is a multiplicity of volume fraction constituents.

15. A method as claimed in claim 14, and wherein the multiplicity of volume fraction constituents includes a liquid and a gas.

16. The method of claim 1 and further comprising:

calculating a permittivity of the at least one condensate with the computer, by utilizing the calculated resonance points of the at least one condensate, and utilizing the known and predetermined information stored in the database, to identify the at least one condensate.

17. The method of claim 1 and wherein the probe is a through probe.

18. A method for identifying and characterizing a transient and periodic condensate entrained in a fluid comprising:

determining a dielectric constant of a condensate moving through a pipe by determining a time delay between an electrical pulse emission into a probe exposed, at least in part, to the fluid and a reflection of the electrical pulse emission from the probe; correlating the determined time delay to a database of known dielectric constants of known condensates to identify the condensate;

applying a Fast Fourier Transform to the determined time delay to generate frequency resonance points of the condensate;

correlating the generated frequency resonance points of the condensate to a database of known resonance points of known condensates and known concentrations of condensates to identify the condensate; and providing a user interface which generates a user perceivable output which identifies the condensate in the fluid in a user perceivable form.

19. The method of claim 18 and further comprising:

providing a pipe having a known interior diameter that communicates with the source of the fluid so that a volume of the fluid moves through the pipe at a velocity; providing a second probe exposed at least in part to the fluid moving through the pipe a known distance downstream from the first probe;

generating a first output by the first probe when a condensate is sensed by the first probe and generating a second output by the second probe when the same condensate is sensed by the second probe, and communicating the first and second probe outputs to the computer;

determining a volume of the condensate moving through the pipe by unit of time by calculating a time difference between the first probe output and the second probe output to determine the velocity of the fluid moving through the pipe; and correlating the determined resonance points of the condensate with the database of known resonance points of concentrations of condensates to determine the volume of the condensate moving through the pipe.

\* \* \* \* \*